United States Patent
Liu et al.

(10) Patent No.: US 10,124,338 B2
(45) Date of Patent: Nov. 13, 2018

(54) MICROBUBBLE GENERATOR DEVICE, SYSTEMS AND METHOD TO FABRICATE

(71) Applicant: IMEC VZW, Leuven (BE)

(72) Inventors: Chengxun Liu, Kessel-Lo (BE); Peter Peumans, Herfelingen (BE); Liesbet Lagae, Leuven (BE); Bivragh Majeed, Lubeek (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 15/526,922

(22) PCT Filed: Nov. 19, 2015

(86) PCT No.: PCT/EP2015/077164
§ 371 (c)(1),
(2) Date: May 15, 2017

(87) PCT Pub. No.: WO2016/079269
PCT Pub. Date: May 26, 2016

(65) Prior Publication Data
US 2017/0341078 A1    Nov. 30, 2017

(30) Foreign Application Priority Data

Nov. 19, 2014 (EP) .................................. 14193831

(51) Int. Cl.
*B07C 5/00* (2006.01)
*B01L 3/00* (2006.01)
(Continued)

(52) U.S. Cl.
CPC . *B01L 3/502761* (2013.01); *B01L 2200/0652* (2013.01); *B01L 2300/0645* (2013.01);
(Continued)

(58) Field of Classification Search
CPC ..... B01L 2200/0652; B01L 2300/0645; B01L 2300/1827; B01L 2400/0442; B01L 2400/067
(Continued)

(56) References Cited

U.S. PATENT DOCUMENTS

| | | | |
|---|---|---|---|
| 7,157,274 B2* | 1/2007 | Bohm | B07C 5/34 209/172.5 |
| 2004/0115830 A1* | 6/2004 | Touzov | B01F 5/061 436/180 |

(Continued)

FOREIGN PATENT DOCUMENTS

| | | | |
|---|---|---|---|
| WO | 2010/147078 A1 | 12/2010 | |
| WO | WO-2010147078 A1 * | 12/2010 | ........ B01L 3/502761 |

OTHER PUBLICATIONS

Takeuchi, Shoji, "Method for Manipulating Particles, and Microfluidic Device", Dec. 23, 2010, Translation (Year: 2010).*

(Continued)

*Primary Examiner* — Terrell H Matthews
(74) *Attorney, Agent, or Firm* — McDonnell Boehnen Hulbert & Berghoff LLP

(57) ABSTRACT

The present disclosure relates to microbubble generator devices for deflecting objects in a liquid, systems for sorting objects that utilize such devices, and methods for fabricating such devices. At least one embodiment relates to a microfluidic device for deflecting objects in a liquid. The device includes a substrate for providing an object-containing liquid thereon. The device also includes a microbubble generator that includes at least one microbubble generating element. The microbubble generator is located on a surface of the substrate and in direct contact with the object-containing liquid when the object-containing liquid is provided on the substrate. The at least one microbubble gener- (Continued)

ating element is configured to deflect a single object in the object-containing liquid through generation of a plurality of microbubbles.

20 Claims, 13 Drawing Sheets

(51) Int. Cl.
G01N 15/10 (2006.01)
G01N 15/14 (2006.01)

(52) U.S. Cl.
CPC .............. B01L 2300/0864 (2013.01); B01L 2300/1827 (2013.01); B01L 2400/046 (2013.01); B01L 2400/0442 (2013.01); B01L 2400/06 (2013.01); G01N 2015/1006 (2013.01); G01N 2015/149 (2013.01)

(58) Field of Classification Search
USPC ....................................... 209/552
See application file for complete search history.

(56) References Cited

U.S. PATENT DOCUMENTS

| | | | |
|---|---|---|---|
| 2004/0183865 A1* | 9/2004 | Hu | B41J 2/14137 347/63 |
| 2006/0128006 A1* | 6/2006 | Gerhardt | B01L 3/502761 435/287.1 |
| 2008/0087584 A1* | 4/2008 | Johnson | B01L 3/502761 209/606 |
| 2009/0032401 A1* | 2/2009 | Ronaghi | B01L 3/502761 204/549 |
| 2010/0006441 A1* | 1/2010 | Renaud | B01L 3/502746 204/643 |
| 2015/0140545 A1* | 5/2015 | Johnson | C12N 5/0081 435/3 |
| 2015/0260181 A1* | 9/2015 | Harvey | F04B 19/006 417/410.1 |

OTHER PUBLICATIONS

PCT International Search Report and Written Opinion, PCT International Application No. PCT/EP2015/077164, dated Mar. 2, 2016, 10 pages.

* cited by examiner

MICROBUBBLE GENERATOR DEVICE, SYSTEMS AND METHOD TO FABRICATE

CROSS-REFERENCE TO RELATED APPLICATION

The present application is a national stage entry of PCT/EP2015/077164 filed Nov. 19, 2015, which claims priority to European Patent Application No. 14193831.6 filed on Nov. 19, 2014, the contents of each of which are hereby incorporated by reference.

FIELD OF THE DISCLOSURE

The field of the disclosure is micro-fluidic devices. In particular, the disclosure is related to jet flow generators for micro-fluidic systems. More in particular, the disclosure is related to flow cytometry devices.

BACKGROUND

Cell sorting is a technique whereby cells are separated based on their properties. Typically, in a first stage, cells propagate through a fluidic channel and are characterized, for example based on size. In a second stage, based on the characterization of each cell, each cell is sorted by deflecting that cell towards an outlet of the fluidic channel.

In alternate devices the deflection of cells is performed by generating a microbubble which creates a jet flow in the fluidic channel. The magnitude of the force of the jet flow on a cell determines to which outlet of the fluidic channel the cell is deflected.

A first problem in these alternate devices is the time to generate a microbubble. Because cell sorting applications include high throughput, it is essential that microbubbles can be generated in a short span of time to keep up with the velocity of cells propagating through the fluidic channel.

A second problem relates to the temperature used to create microbubbles. To bring a liquid to its boiling point on a micro scale, a higher temperature is used than the boiling temperature of bulk liquid. This phenomenon is known as superheating. The use of higher temperatures leads to higher energy consumption and, related to the first problem, to a longer duration of the heating to create microbubbles.

A third problem relates to the accuracy of the sorting. The accuracy is related to the controllability of the generated microbubbles. In order to increase the accuracy, total control over the force created by the jet flow can be used. In alternate devices, this is lacking.

There is an opportunity for a micro-fluidic device which solves at least some of the problems stated above.

SUMMARY

Some embodiments create a microbubble generator which allows accurate generation of a jet flow in a liquid.

Particular aspects are set out in the accompanying independent and dependent claims. Features from the dependent claims may be combined with features of the independent claims and with features of other dependent claims as appropriate and not merely as explicitly set out in the claims. Embodiments of the micro-bubble generator are discussed in claims 1 to 13. In claims 14 to 16 embodiments of systems for sorting objects such as cells, using the micro-bubble generator, are discussed. In claims 17 to 22, embodiments of methods for fabricating a microbubble generator are discussed.

It some embodiments, a microbubble generator may be provided that generates microbubbles in a very short span of time thereby making it useful for sorting objects such as cells at high speed, e.g. at least 10.000 cells/s. Hence, in some embodiments, a cell sorting system is provided enabling such high throughput. In some embodiments, a microbubble generator may be provided that is inexpensive and easy to fabricate. In some embodiments, a microbubble generator may be provided that may be fabricated using semiconductor technology, e.g. CMOS compatible processing steps.

In a first aspect, a micro-fluidic device for deflecting objects in a liquid may be provided, comprising:
a substrate for providing thereon an object-containing liquid; and
a microbubble generator, having at least one microbubble generating element located on a surface of the substrate and in direct contact with the liquid when provided on the substrate;
characterized in that:
the at least one microbubble generating element is adapted to deflect a single object in the liquid through generation of a plurality of microbubbles by each of them.

According to example embodiments, the at least one microbubble generating element comprises a first series of connected microstructures; each microstructure adapted for generating a microbubble in the liquid when the microbubble generator is activated.

According to example embodiments, the microbubble generator may be a heating element and the at least one microbubble generating element may be at least one micro-heater located on a surface of the substrate and in direct contact with the liquid when provided on the substrate, characterized in that the at least one micro-heater is adapted to deflect a single object in the liquid through the generation of a plurality of microbubbles by each of the micro-heaters.

Other embodiments may provide microbubbles by other methods, like cavitation. For example, embodiments may comprise an electrolytic unit as microbubble generator, comprising at least one set of electrodes with the function of a microbubble generating element. In this case, activating a microbubble generator may comprise inducing a voltage in the electrolytic unit, for example. The electrodes may be shaped such that at least two microstructures generate microbubbles simultaneously when a voltage is applied to the electrodes.

According to example embodiments, the at least one microbubble generating element is adapted so at least two microstructures are activated when the microbubble generating element is activated. In embodiments comprising a micro-heater, the micro-heater is shaped such that at least two microstructures heat up simultaneously when an electrical current flows through the at least one micro-heater.

According to example embodiments, the at least one micro-heater further comprises a second series of connected microstructures connected in parallel to the first series of connected microstructures; and the at least one micro-heater is shaped such that at least two microstructures of different series of connected microstructures heat up simultaneously when an electrical current flows through the micro-heater.

According to example embodiments, the device further comprises a non-conductive layer, located in between the liquid and the microbubble generator, e.g. the heating element, having a plurality of cavities fabricated down to the microbubble generator, e.g. the heating element, wherein each cavity is aligned with a corresponding microstructure.

According to example embodiments, one of the cavities comprises at least one sharp corner.

According to example embodiments, a cross-section, parallel to the substrate, of one of the cavities is triangular or rectangular shaped.

According to example embodiments, each microstructure comprises a portion having a cross-sectional dimension of 10 micrometers or smaller.

According to example embodiments, the microbubble generator comprises only one conductive, e.g. metal, layer. For example, the conductive layer may be comprised in a heating element.

According to example embodiments, the device further comprises a controller connected to the microbubble generator and configured to monitor a parameter or parameters related to the generation of microbubbles. For example, in embodiments comprising a heating element a microbubble generator and at least one micro-heater as microbubble generating element, the controller may be configured to monitor the temperature of the heating element or configured to monitor the resistance of the heating element. In some embodiments, it may control both temperature and resistance, or any other parameter related to microbubble nucleation and generation. In embodiments comprising an electrolytic unit, the controller may be configured to monitor the voltage, and/or any other parameter related to microbubble generation via electrolysis, such as current or capacitance.

According to example embodiments comprising a heating element as a microbubble generator, the heating element comprises a SiC layer for preventing deformation of the heating element.

In a second aspect, a system for sorting objects is presented, comprising a first micro-fluidic device as described in the above paragraphs and a first micro-fluidic channel; wherein the first micro-fluidic device is positioned to deflect single objects propagating in the first micro-fluidic channel by generating microbubbles.

According to example embodiments, the system further comprises a second micro-fluidic channel fluidically connected to the first micro-fluidic channel; wherein the first micro-fluidic device is positioned in the second micro-fluidic channel and configured for deflecting single objects propagating in the first micro-fluidic channel by generating microbubbles.

According to example embodiments, the system further comprises a third micro-fluidic channel fluidically connected to the first micro-fluidic channel, wherein the second and the third micro-fluidic channel are aligned and positioned at opposite sides of the first micro-fluidic channel; and further comprising a second micro-fluidic device positioned in the third micro-fluidic channel and wherein the first and the second micro-fluidic devices are configured for deflecting single objects propagating in the first micro-fluidic channel.

According to example embodiments of a third aspect, the first and the second microfluidic devices are further configured to synchronously deflect single objects propagating in the first micro-fluidic channel.

A method for fabricating a micro-fluidic device is presented, the method comprising: providing a substrate; providing a conductive, e.g. metal, layer on top of the substrate; patterning a microbubble generator, e.g. a heating element, having at least one microbubble generating element, e.g. at least one micro-heater, in the conductive layer;
characterized in that:

patterning the microbubble generator comprises patterning a microbubble generating element comprising a series of microstructures, wherein each microstructure is adapted for generating a microbubble when activated.

In some embodiments, patterning of the microbubble generator having at least one microbubble generating element may comprise fabricating the at least one microbubble generating element such that its shape allows at least two microstructures of the at least one microbubble generating element to generate microbubbles simultaneously when the at least one microbubble generating element is activated.

According to example embodiments, the patterning of the at least one microbubble generating element may comprise patterning of at least one micro-heater, which comprises fabricating the at least one micro-heater such that its shape allows at least two microstructures of the at least one micro-heater to heat up simultaneously, thereby generating microbubbles, when an electrical current flows through the at least one micro-heater.

According to example embodiments, the patterning of the at least one microbubble generating element may comprise patterning of at least one set of electrodes of an electrolytic unit, which comprises fabricating the at least one set of electrodes such that its shape allows at least two microstructures of the at least one set of electrodes to induce electrolysis simultaneously when a voltage is applied between the electrodes, thereby producing microbubbles.

According to example embodiments, the method further comprises providing a micro-fluidic layer on top of the microbubble generator, e.g. heating element; creating a micro-fluidic channel in the micro-fluidic layer; and closing the micro-fluidic channel with a lid.

According to example embodiments, the micro-fluidics layer is a photo-patternable polymer for attaching the lid.

According to example embodiments, a photo-patternable polymer is present in between the lid and the micro-fluidic layer, for closing the micro-fluidic channel with a lid.

For purposes of summarizing various embodiments, certain objects have been described herein above. Of course, it is to be understood that not necessarily all such objects may be achieved in accordance with any particular embodiment. Thus, for example, those skilled in the art will recognize that the invention may be embodied or carried out in a manner that achieves one object as taught herein without necessarily achieving other objects as may be taught or suggested herein.

The above and other aspects will be apparent from and elucidated with reference to the embodiment(s) described hereinafter.

BRIEF DESCRIPTION OF THE DRAWINGS

Embodiments will now be described further, by way of example, with reference to the accompanying drawings, in which.

Figure 1:
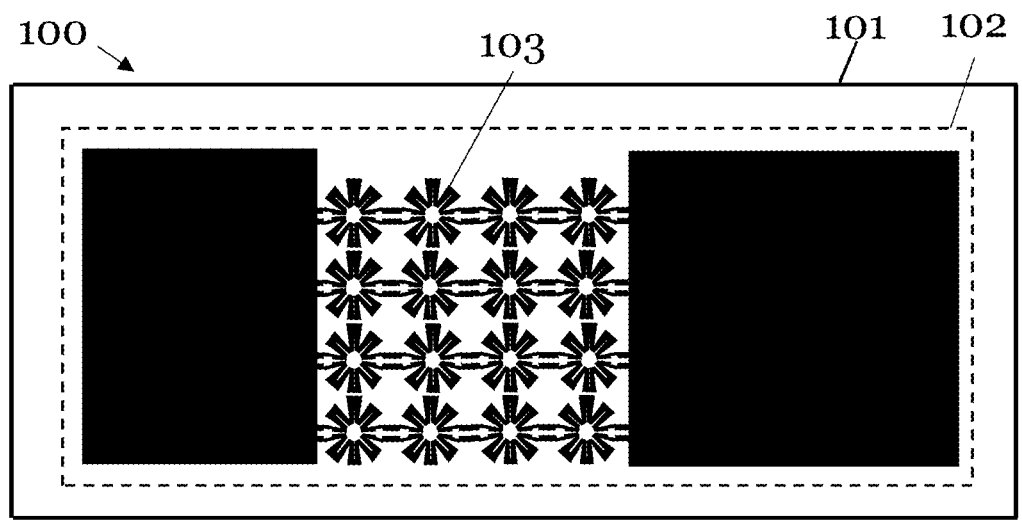
FIG. 1 illustrates a micro-fluidic device, according to example embodiments.

The drawings are only schematic and are non-limiting. In the drawings, the size of some of the elements may be exaggerated and not drawn on scale for illustrative purposes. The dimensions and the relative dimensions do not necessarily correspond to actual reductions to practice.

In the different drawings, the same reference signs refer to the same or analogous elements. Any reference signs in the claims shall not be construed as limiting the scope.

DETAILED DESCRIPTION OF EXAMPLE EMBODIMENTS

The device as presented in this disclosure provides solutions to the problems of alternate devices as described above.

Throughout the description reference is made to "a micro-fluidic device" and "a micro-fluidic device for deflecting objects in a liquid". This may refer to "a micro-bubble generator device" or "a jet flow generator device".

Throughout the description reference is made to "a micro-fluidic channel". This may refer to channels suitable for transporting particles of microscopic size such as cells. The dimensions of these channels, e.g. the width and depth may vary from 10 nm to 100 micrometers.

Firstly, the problem related to the duration of time to generate a jet flow is solved by generating a plurality of microbubbles generated by microstructures, which conjointly create the jet flow. By generating multiple microbubbles instead of generating a single microbubble, the size of the microbubbles used to generate that jet flow can be reduced. The reduced size of the microbubbles use less power to generate these microbubbles. The smaller the microbubble, the lower the energy, for instance the temperature, used to create that microbubble. Thus, a heating element configured to generate a plurality of microbubbles can generate microbubbles faster because it takes less time to bring the heating element to the adequate temperature. Analogously, an electrolytic unit configured to generate a plurality of microbubbles may generate also microbubbles faster by applying a small voltage. Such a device may provide a faster response time when it is triggered, for example by supplying a current or voltage pulse to the microbubble generator, compared to systems using a large microbubble to create the jet flow.

This may be useful when the device is used in an in-flow cell sorting device. The faster the response time, the higher the velocity of objects in the cell sorting device can be, resulting in a higher throughput. Power consumption can be reduced because of the lower energy used to generate microbubbles. For example, lower temperature may be used in a heating element, or a lower voltage may be used in an electrolytic unit. This is useful for on-chip cell sorting devices because of the highly parallelized architecture which comprises a plurality of devices for sorting cells, all of which can be connected to a power supply.

Secondly, the problem related to the energy used to create microbubbles is solved by using a layer comprising multiple structures, also known as artifacts, which are aligned with microstructures adapted to generate the plurality of microbubbles. For example, it solves the problem of superheating in the case of heating elements, and may reduce the amount of voltage used to nucleate a stable microbubble (e.g. a bubble that does not detach) in the case of electrolytic units for microbubble generation. When a surface is smooth, in the case of heating elements, superheat is considerably high, demanding approximately 350° C. for water vapor microbubble nucleation. The superheat, however, can be drastically reduced by surface artifacts (defects) or artificial micro structures serving as microbubble nucleation centers. The artifacts are irregularities, for example cavities, in the layer which contribute to the reduction of the superheat in case of heating elements. Whereas a relative high temperature is used to create microbubbles in a liquid, this temperature is reduced by providing this layer on top of these microstructures. The reduction of the superheat allows microbubbles to be generated at lower temperatures. Again, a lower temperature means that the duration of time used to bring the heating element to the adequate temperature is reduced. Thus, a device having such a layer features a faster response time. Likewise, an electrolytic unit uses a determined voltage necessary to generate microbubbles, but these tend to detach at small sizes. Additional artifacts on the surfaces help in microbubble nucleation, obtaining a minimum amount of microbubbles on the surface for a lower voltage, hence reducing the risk of microbubble detachment.

Thirdly, the problem related to the accuracy of the sorting is solved by simultaneously creating a plurality of microbubbles instead of creating a single microbubble to create the jet flow. Also, large microbubbles can take a much longer time to collapse compared to small microbubbles because of the smaller surface/volume ratio, thus resulting in long microbubble life time and low sorting throughput. The process of generating small microbubbles is more controllable than the creation of a single larger microbubble. Therefore, a jet flow created by a plurality of microbubble can be accurately controlled. In cell sorting micro-fluidic devices this may be useful because cells propagating through micro-fluidic channels may be deflected by such a jet flow. An increased control over the force created by the jet flow translates into an increased accuracy of the sorting. Also, the increased control allows the use of smaller microfluidic channels. Hence, more microfluidic channels may be fabricated in certain area.

In a first aspect, a micro-fluidic device for generating microbubbles in a liquid is presented. The micro-fluidic device is adapted to deflect objects in a fluid. These objects may be particles, for example particles of a biological nature such as cells or smaller sized particles.

Embodiments are firstly described hereinafter in more detail with reference to the microbubble generator being a heating element, and the at least one microbubble generating element being at least one micro-heater. This, however, is not intended to be limiting, as also other types of microbubble generators may be used, as described in more detail with respect to a second embodiment.

First Embodiment

FIG. 1 shows an example of micro-fluidic device 100 comprising a heating element 102 as a microbubble generator, comprising at least one micro-heater 103 as microbubble generating element, the at least one micro-heater 103 comprising a plurality of microstructures 104 as microbubble nucleation or generation sites. The micro-fluidic device 100 comprises a substrate 101 for providing a liquid on. A heating element 102 comprising at least one micro-heater 103 is located on a surface of the substrate 101. The at least one micro-heater 103 is in direct contact with the liquid when it is provided on the substrate 101. The at least one micro-heater 103 is designed such that it can generate a force in the liquid by displacing a part of the liquid. The displacement of a part of the liquid is performed by generating a plurality of micro-bubbles. Hence, a flow is created. The force of the flow in the liquid, caused by the ensemble of generated microbubbles, is suitable to deflect objects present in the liquid. Thus, the at least one micro-heater 103 is adapted to deflect a single object in the liquid by creating a force in the liquid through generation of a plurality of microbubbles.

An embodiment of the first aspect is illustrated in FIG. 1. The micro-fluidic device 100 comprises a substrate 101. A heating element 102 positioned on a surface of the substrate 101. The heating element 102 is located on the surface of the substrate 101 on which a liquid may be provided. When a liquid is provided, the heating element is in direct contact with the liquid. The substrate 101 may be a semiconductor substrate, e.g. a silicon substrate. The substrate 101 may also be a glass substrate. The substrate 101 may be an inner wall of a micro-fluidic component, for example an inner wall of a micro-fluidic channel. The heating element 102 may be located on any inner wall of a micro-fluidic component, as long as the heating element 102 is in contact with a liquid when present in the micro-fluidic component. The heating element 102 is fabricated from a conducting material such as a metal, e.g. aluminum, copper, tungsten or polysilicon. The heating element 102 may be fabricated from a single metal layer. For example, the thickness of the heating element 102 can be minimized and fabrication of the device can be simplified thereby reducing cost to manufacture as no additional metal layers are used. Embodiments are not limited to metal layers, and any other conductive materials (such as heavily doped semiconductors) can be used.

Figure 2:
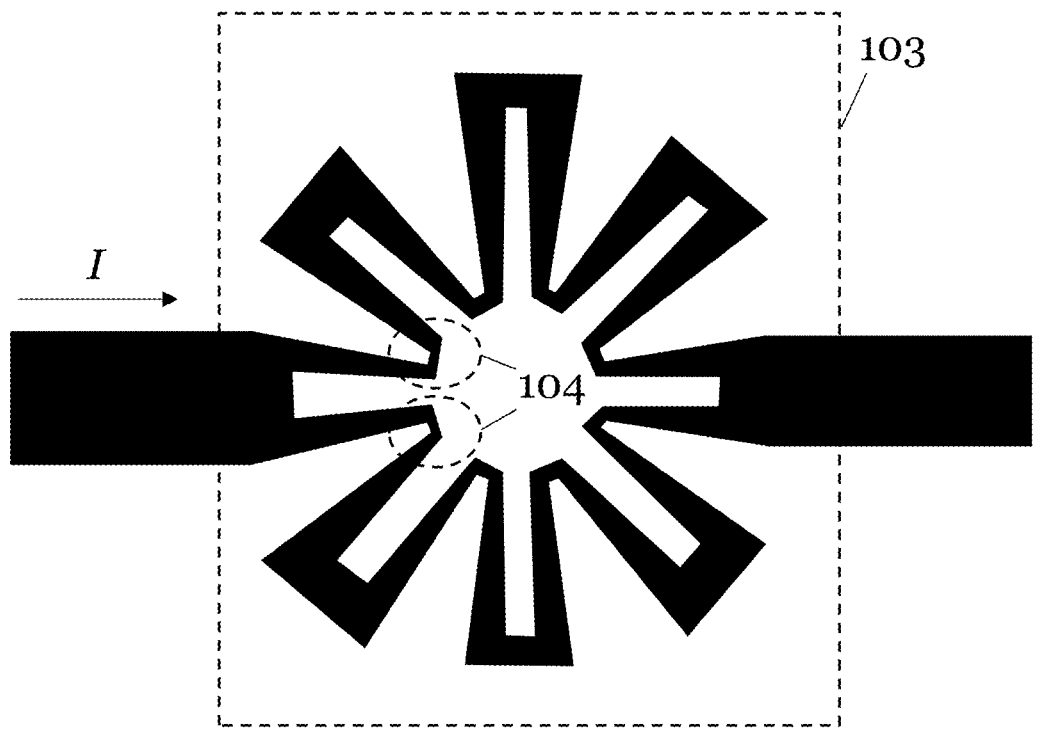
FIG. 2 illustrates a single micro-heater, according to example embodiments.

The heating element 102 comprises at least one micro-heater 103 adapted for generating a plurality of microbubbles in a liquid. An embodiment of a micro-heater is illustrated in FIG. 2. The at least one microheater 103 is a structure which is fabricated in a conductive, e.g. a metal, layer comprising the heating element 102. For the purpose of generating a plurality of microbubbles per micro-heater 103, each micro-heater 103 comprises a plurality of microstructures 104. Each microstructure 104 is a feature of the micro-heater 103 and is a part of the heating element 102. Each microstructure 104 is adapted to generate a microbubble in a liquid when the micro-heater 103 heats up. This adaptation comprises that dimensions, e.g. the width or height, of each microstructure 104 are smaller than the dimensions, e.g. the width or height, of the rest of the microheater 103. The selected dimensions ensure that microbubbles are generated at dedicated spots of each microheater 103, each spot being the location of a microstructure 104. The microstructures are thermally favored for microbubble creation because of the locally higher current density hence causing joule heating. For example, this assurance contributes to controllability of generated microbubbles by the microfluidic device 100. It can be accurately determined at which location a microbubble will be generated. According to example embodiments, a microstructure 104 may have a cross-sectional dimension, e.g. a width, of 10 micrometers or smaller. This means that dimensions of other parts of the micro-heater 103 are larger than 10 micrometers to ensure that microbubbles are generated at the location of the microstructures 104.

The plurality of microstructures 104 of a single microheater 103 may be a first series of electrically connected microstructures. Thus, the plurality of microstructures 104 may be an array of microstructures 104 which are connected in series. The first series of electrically connected microstructures may be a meander shaped structure, e.g. a meander shaped wire, wherein specific portions of the structure have smaller dimensions than the rest of the structure, each portion being defined as a microstructure. The parts may be turns of the meander shaped structure, for example alternate turns. The meander shaped structure may be shaped such that a maximum number of turns can be achieved in a predefined area. By using such a structure, a maximum number of microbubbles can be generated on a given area. Hence, compactness of the device is increased allowing it to be used inside micro-fluidic channels. In the single micro-heater 103, a second series of electrically connected microstructures may be electrically connected in parallel to the first series of electrically connected microstructures. A single meander shaped micro-heater 103 is illustrated in FIG. 2.

According to example embodiments, each micro-heater 103 is a circular meander shaped structure having a plurality of microstructures 104. Each microstructure 104 may be located at an even distance from a central point of the micro-heater 103.

According to example embodiments, each micro-heater 103 comprises at least two microstructures 104 which are electrically connected in parallel. According to example embodiments, the micro-fluidic device 100 may comprise a series of micro-heaters, electrically connected in series. Further, the micro-fluidic device 100 may comprise a plurality of series of micro-heaters, electrically connected in parallel. The plurality of series of micro-heaters may be positioned staggered for achieving homogeneous distribution of the heat and increasing stability of the microbubble generation and control over the force generated by the microbubbles.

Figure 3:
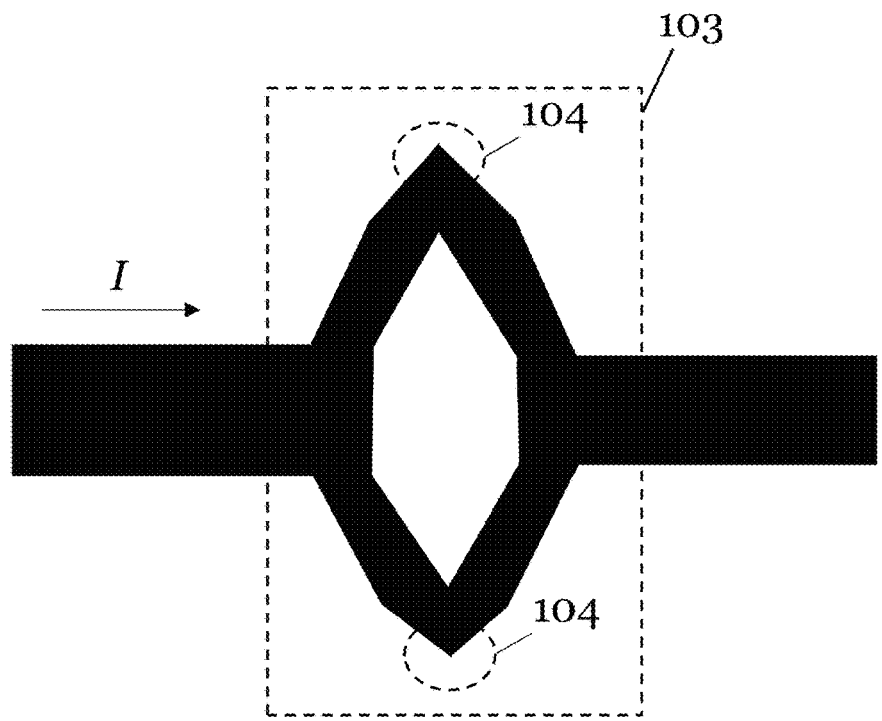
FIG. 3 illustrates a single micro-heater, according to example embodiments.

According to example embodiments, each micro-heater 103 is lip-shaped. Such a shape is illustrated in FIG. 3. The two outer sharp corners of the lip-shaped structure are two microstructures 104. In such an embodiment, the micro-heater 103 has a first and a second curved portion. Both portions are curved away from each other thereby forming a cavity in the middle (both portions are unconnected at the cavity). One end of the first curved portion is only connected to one end of a second curved portion thereby forming a sharp tip. The other end of the first curved portion is only connected to the other end of the second curved portion thereby forming a sharp tip. By connecting both portions, a lip-shaped micro-heater 103 is formed having two sharp tips (which are the microstructures 104). Because the microstructures 104 are located at both ends of the lip-shaped micro-heater 103, heat generated in one microstructure 104 may not influence the other. This allows for a homogeneous distribution of the heat and therefore an increased stability of the microbubble generation and control over the force generated by the microbubbles.

Figure 5:
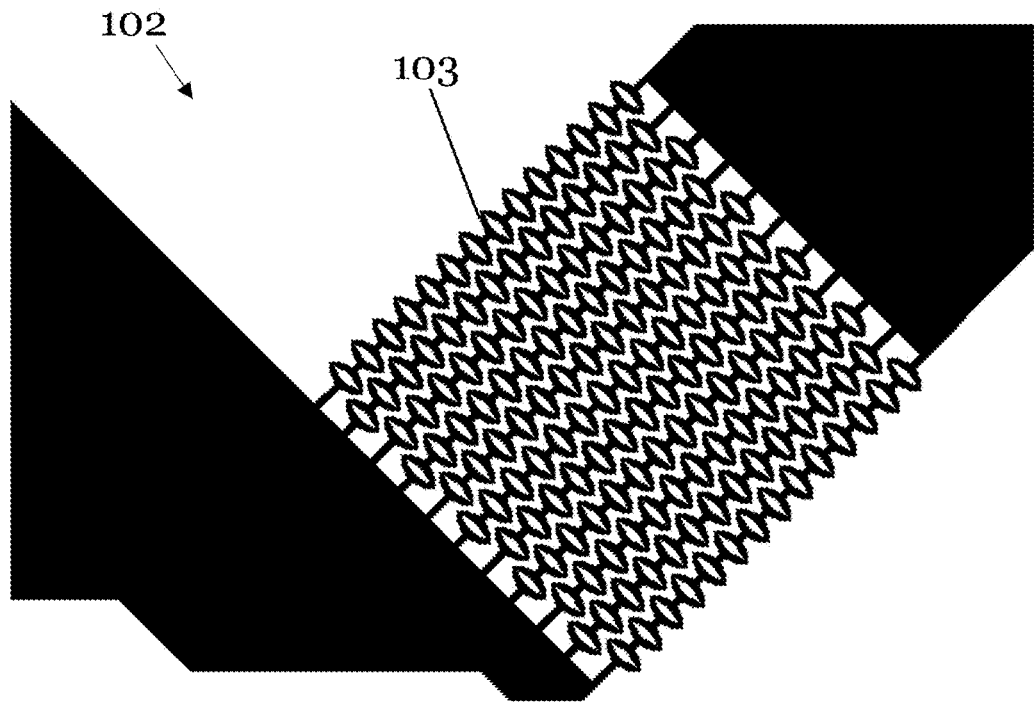
FIG. 5 illustrates a matrix of microbubble generating elements according to example embodiments.

When the heating element 102 comprises a plurality of lip-shaped micro-heaters 103, the lip-shaped micro-heaters 103 can be positioned staggered. This is illustrated in FIG. 5. For example, more microheaters 103 can be positioned on a given area. In semiconductor devices this allows for a reduction of silicon material which decreases the cost of the device. Also, when more micro-heaters 103 can be positioned in the same area, a jet flow can be generated with smaller microbubbles. Hence, the jet flow can be created faster and with better control which contributes to a higher cell sorting throughput.

Figure 6:
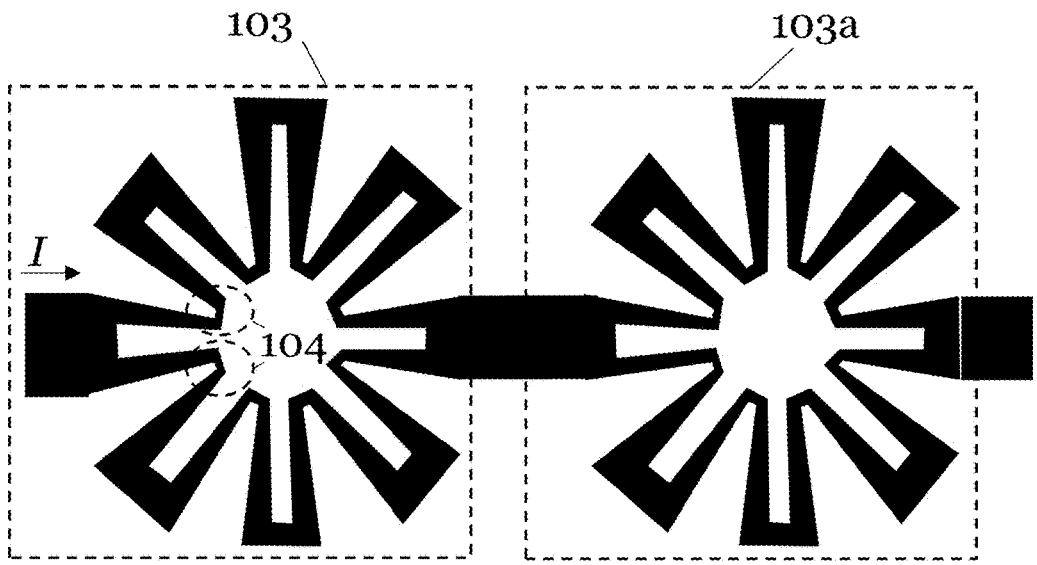
FIG. 6 illustrates two micro-heaters, according to example embodiments.

A plurality of micro-heaters 103, 103*a* may be electrically connected to each other in series. Such an embodiment is illustrated in FIG. 6. When a voltage pulse is supplied to the heating element, an electrical current flows through each micro-heater 103, 103*a* causing each micro-heater to heat up. When a liquid is present on the heating element, a plurality of microbubbles are generated in the liquid when the micro-heaters 103, 103*a* reach an adequate temperature, e.g. 350 degrees Celsius.

Figure 7:
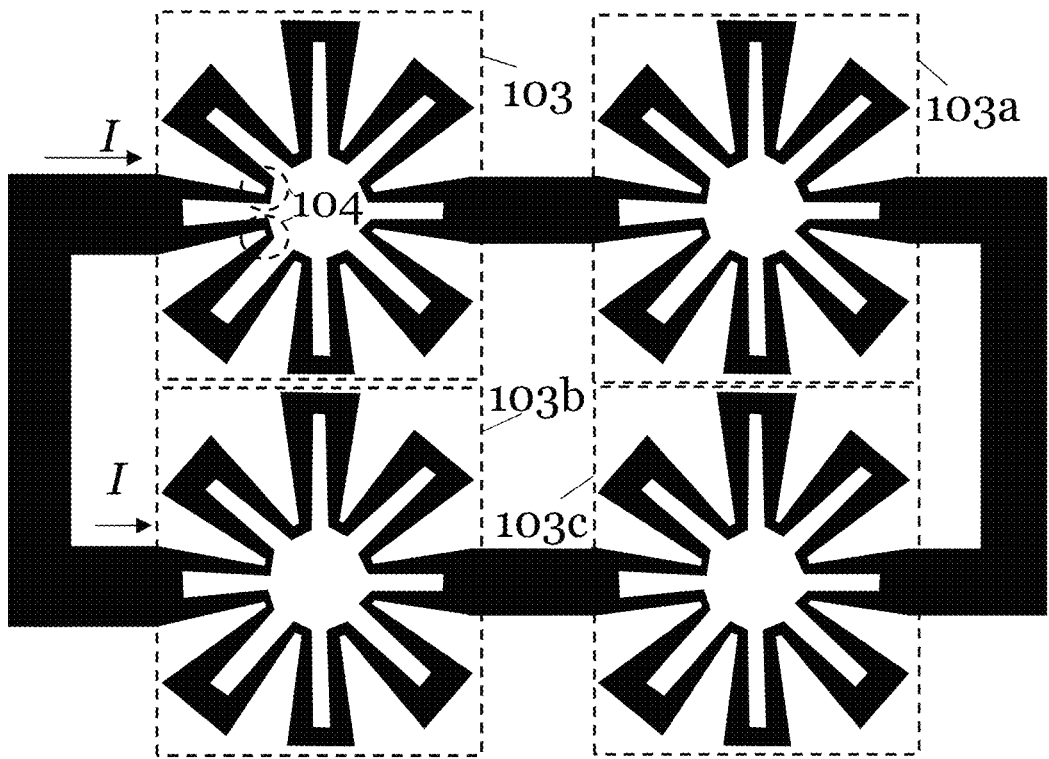
FIG. 7 illustrates of a matrix of micro-heaters, according to example embodiments.

In addition, a plurality of micro-heaters 103, 103*a*, 103*b*, 103*c* may be electrically connected, in parallel. The plurality of micro-heaters may be a matrix of micro-heaters 103, 103*a*, 103*b*, 103*c*. Such an embodiment is illustrated in FIG. 7. In some embodiments, micro-heaters may generate microbubbles simultaneously thereby contributing to increased controllability of microbubbles. Also, a plurality of microbubbles can be generated in a small area. This may be useful in dense micro-fluidic systems having a plurality of micro-fluidic channels, each comprising a micro-fluidic device as described herein.

According to example embodiments, the micro-fluidic device comprises at least one row of interconnected microbubble generating elements, e.g. micro-heaters. The micro-fluidic device may also comprise adjacent rows of interconnected micro-heaters. Hence, the micro-fluidic device comprises a matrix of micro-heaters. In some embodiments, multiple micro-heaters may simultaneously create microbubbles thereby contributing to increased controllability of a jet force created by the micro-fluidic device.

According to example embodiments, each micro-heater is shaped such that at least two microstructures 104 of a single micro-heater 103 heat up simultaneously when an electrical current flows through the micro-heater. This is achieved by for example positioning the microstructures 104 symmetrically, e.g. circular, around a central point of the micro-heater 103, for example by positioning the microstructures at even distances from that central point. In such an embodiment, each micro-heater 103 may be star-shaped. When an electrical current flows through the micro-heater 103, the current flows simultaneously through different parts of the micro-heater 103 thereby causing simultaneous heat up of different microstructures 104.

Figure 8:
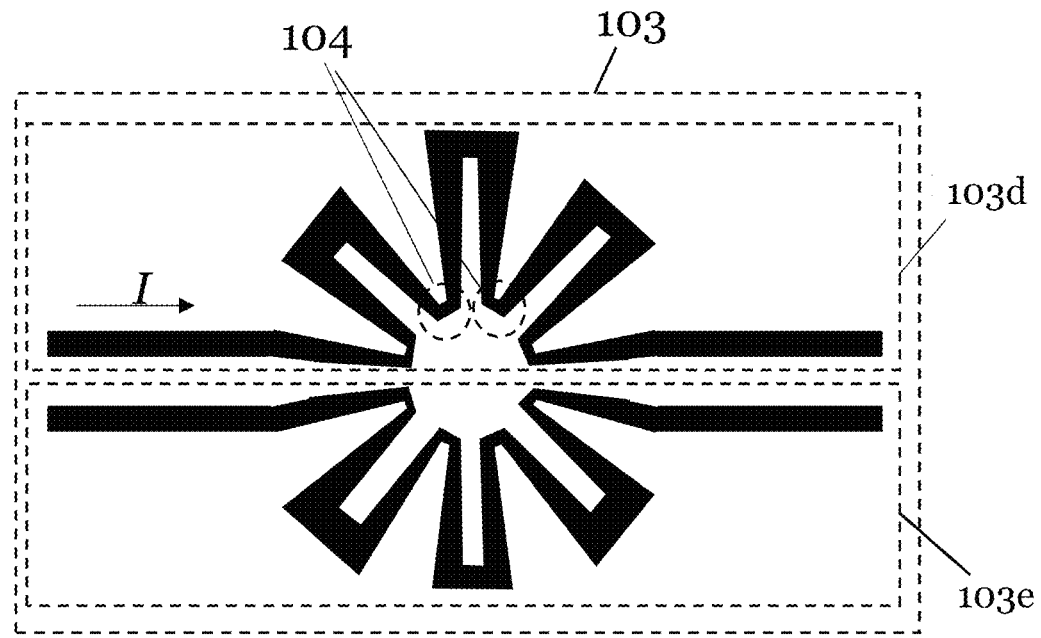
FIG. 8 illustrates a single micro-heater, according to example embodiments.
Figure 9:
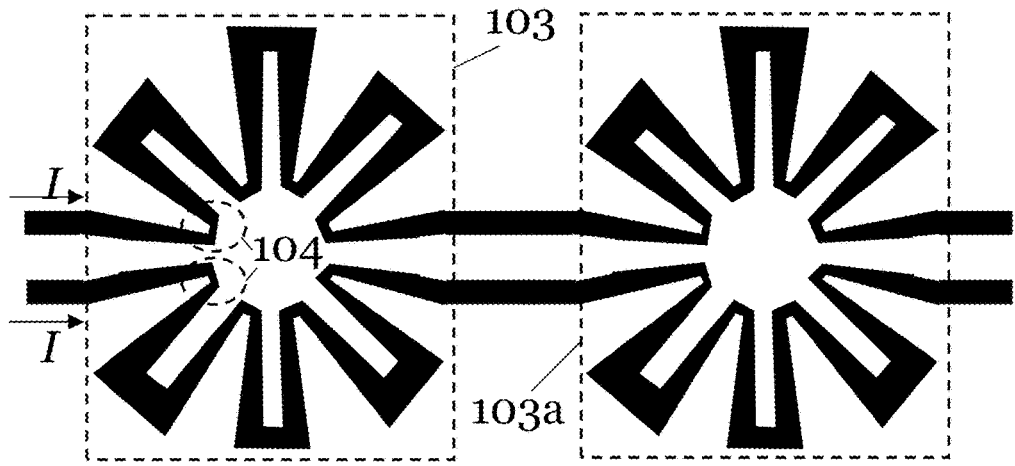
FIG. 9 illustrates two micro-heaters, according to example embodiments.
Figure 10:
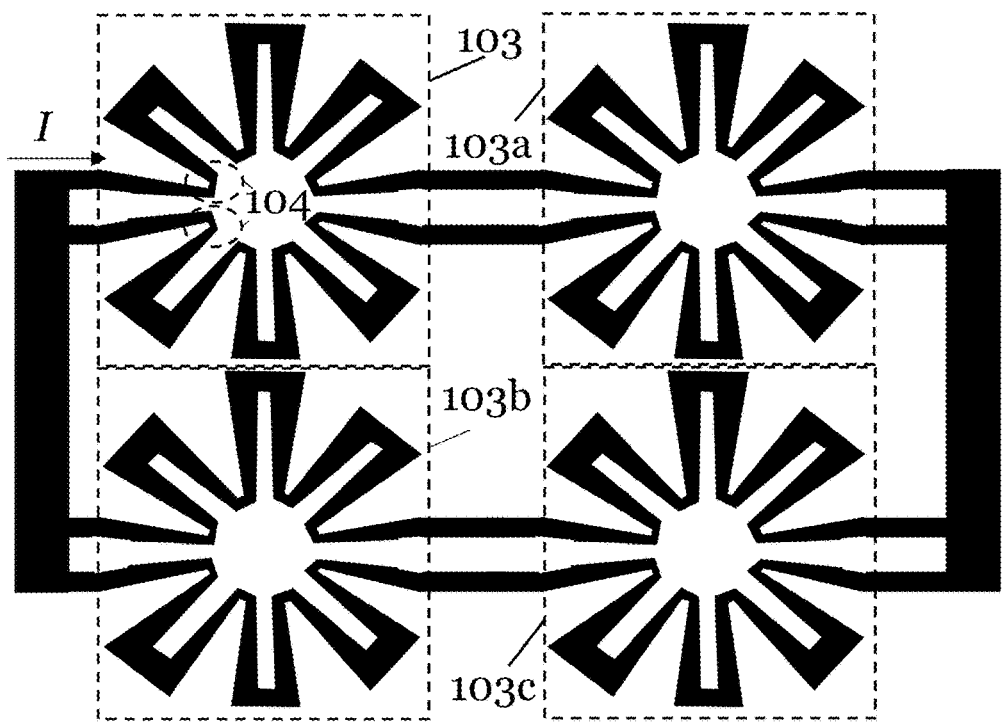
FIG. 10 illustrates a matrix of micro-heaters, according to example embodiments.

A single micro-heater 103 may also comprise different series of electrically connected microstructures 104 which are unconnected at the level of the micro-heater 103 but connected at the level of the heating element 102. Such an embodiment is illustrated in FIG. 8. In FIG. 8, a single micro-heater 103 is illustrated having two series of structures 103*d*, 103*e*. The two series 103*d*, 103*e* are unconnected at the level of the micro-heater. Different micro-heaters may be connected in series to each other thereby forming a chain of micro-heaters. Such an embodiment is illustrated in FIG. 9. Two micro-heaters 103, 103*a* are connected to each other. A first series of microstructures 104 of a first micro-heater 103 is connected to a first series of microstructures 104 of a second micro-heater 103*a*. A second series of microstructures 104 of the first microheater 103 are connected to a second series of a second micro-heater 103*a*. In such an embodiment, a microheater may be shaped such that at least two microstructures 104 of different series of connected microstructures 104 heat up simultaneously when an electrical current flows through the micro-heater 103. As described above, in another embodiment, different micro-heaters of the heating element 102 may be connected to each other in parallel. Such an embodiment is illustrated in FIG. 10.

A shielding layer on top of the microbubble generator may be provided for shielding at least partially the microbubble generation sites from the liquid.

In an example embodiment, the heating element 102 may be covered with a shielding layer for shielding the micro-heaters 103 of the heating element 102 from the liquid. The layer may be fabricated from electrically insulating material such as $SiO_2$ or SiN, having a sufficient thickness such as between 20 nm and 2 µm, e.g. 350 nm. Thus, there is no direct contact between the heating element and a liquid. The thickness of the shielding layer is adapted thereby allowing heating up of a liquid to generate microbubbles in that liquid.

In some embodiments comprising heating element 102 fabricated from a single metal layer, it was surprisingly observed that after several voltage or current pulses were supplied to the micro-heaters 103 to induce thermal vapor microbubbles, the microstructures 104 underwent a structural change. This is illustrated in the four SEM images (a), (b), (c) and (d) of FIG. 12.

The upper-left image (a) is a SEM image of a microheater before supplying voltage or current pulses. The lower-left image (b) is a SEM image of a micro-heater after supplying voltage or current pulses. In the lower-left image (b) it can be noticed that an artifact 120 is formed at each microstructure 104. The upper-right image (c) is a SEM image of an individual microstructure 104. The artifact 120 being formed at a sharp corner of the microstructure 104 after voltage or current pulses are supplied to the microheater is illustrated in lower-right image (d).

Figure 12:
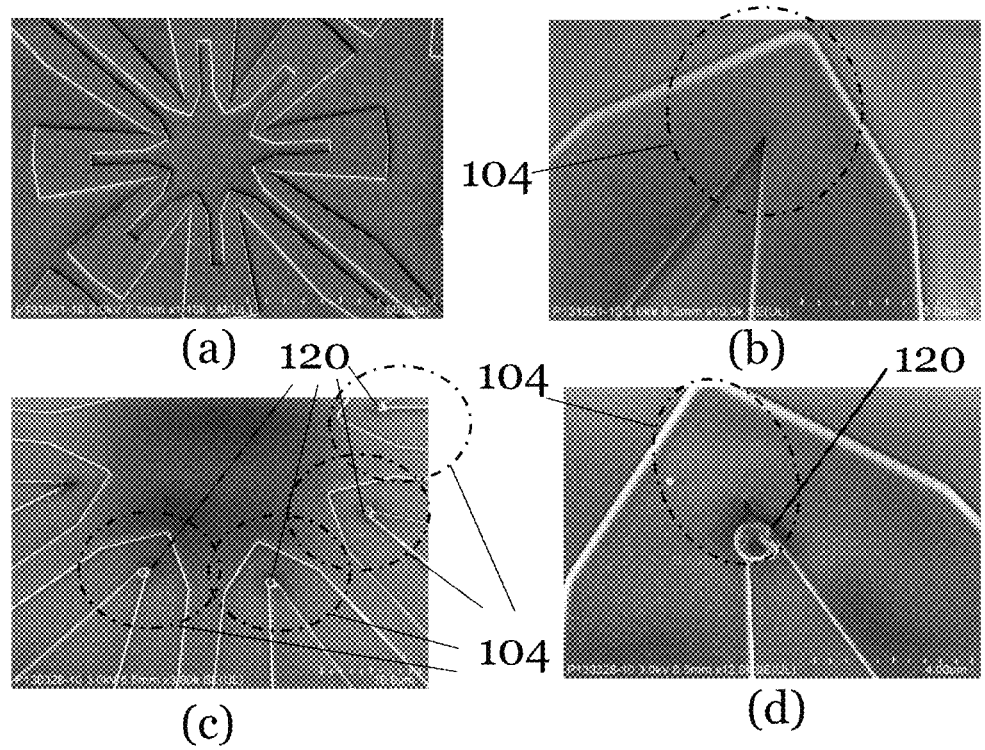
FIG. 12 are SEM images of a micro-heater and a microstructure, according to example embodiments.

The deformation of the microstructures may create artifacts which contribute to a reduction of the superheat. Each artifact can be considered as a self-induced nucleation center contributing to the reduction of superheat. These artifacts may reduce the amount of power used for microbubble generation at the microstructures (approximately 10-15% from experimental findings) and the device's life time is thereby extended. The deformation may be caused by the metal of the microstructures being thermally deformed or by electro-migration. This cyclic deformation takes place at every heating pulse, and finally produces irreversible structural deformation. The deformation also propagates to the adjacent shielding layer on top of the metal, thus leading to the artifact visible in the SEM picture. On the other hand, the deformation may also be take place in the shielding layer during the supply of voltage or current pulses, or it may take place by other methods such as deposition, etching, mechanical action, or any other suitable methods. The device as illustrated in FIG. 12 uses aluminum as metal for the heating element and $SiO_2$ as a shielding layer.

Devices where deformation takes place are interesting to use in low-power devices because of the reduction of the superheat. Such devices may be used in e.g. disposable devices because of their short-term usage and low cost as less materials are used and it is easier to manufacture. Embodiments are not limited to deformations in the metal, and they may be present in general in the conductive layer, or not be present at all.

When long term usage is envisaged, the device may further comprise a robust capping layer. According to example embodiments, the capping layer is positioned on top of the heating element 102. The capping layer may comprise silicon carbide, e.g. may be a SiC layer. The SiC prevents deformation of the heating element. SiC may be used as it is thermally and chemically stable, thermally more conductive than $SiO_2$ or SiN, and it may be deposited as a smoother surface with fewer uncontrolled artifacts.

In spite of the aforementioned thermal & mechanical properties, SiC is not an optimized material for electrical insulation. The resistivity is around 1e3 ohm cm, and decreases at higher temperatures. Thus, a sole SiC capping layer cannot be placed directly above the conductive heating elements. To electrically insulate the conductive layer of the heating element from the SiC layer, the aforementioned shielding layer is present in between. As discussed earlier, the shielding layer may be an electrically insulating layer such as e.g. a $SiO_2$ and/or a SiN layer. The shielding layer also contributes to thermal deformation tolerance and control. A suitable material for the shielding layer is SiN, due to its electrical resistivity of approximately 1e15 ohm cm, which is much better than SiC. The SiN layer can be regarded as electrically non-conductive. The SiN layer may have a thickness between 20 nm and 2 micrometers, e.g. 300 nm. Alternatively the buffer layer may be a $SiO_2$ layer having a thickness between 20 nm and 2 micrometers. The thickness of the $SiO_2$ layer may be e.g. 350 nm.

Figure 13:
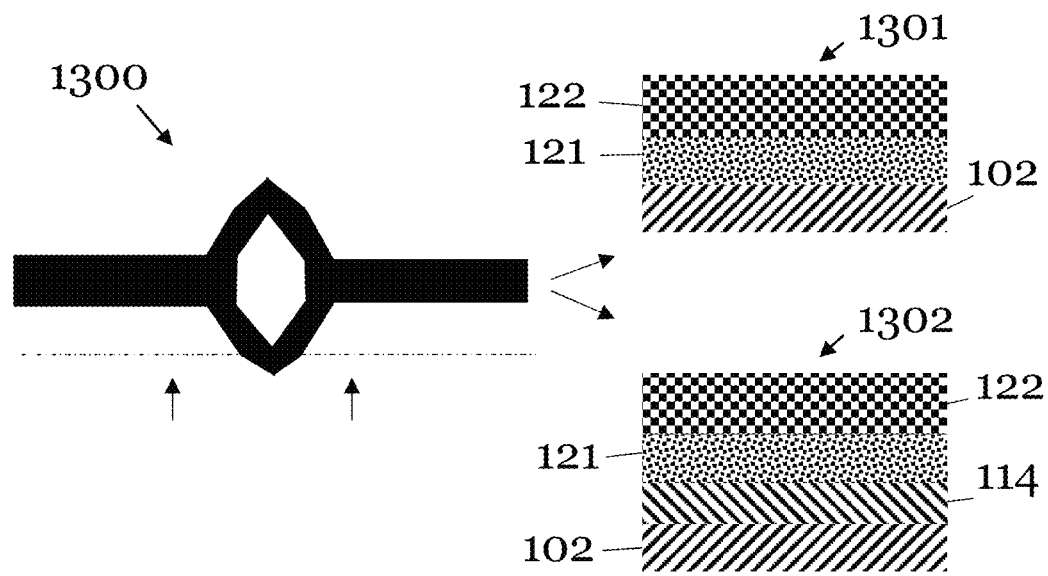
FIG. 13 illustrates a micro-heater and cross-sectional views of a micro-heater, according to example embodiments.

FIG. 13 shows a micro-heater 1300 and two possible cross-sectional views 1301, 1302 of different embodiments of the micro-heater, the position of the cross-section being indicated in 1300 by a dashed line, and the view being indicated by two arrows. In the cross-sectional view 1301, the micro-heater comprises: a conductive, e.g. metal, layer 102, a layer 121 comprising $SiO_2$ or a SiN or a mixture thereof, and a capping layer 122. In the cross-sectional view 1302, the micro-heater comprises: a conductive, e.g. metal, layer 102, a $SiO_2$ layer 114, a SiN layer 121, and a capping layer 122.

Figure 14:
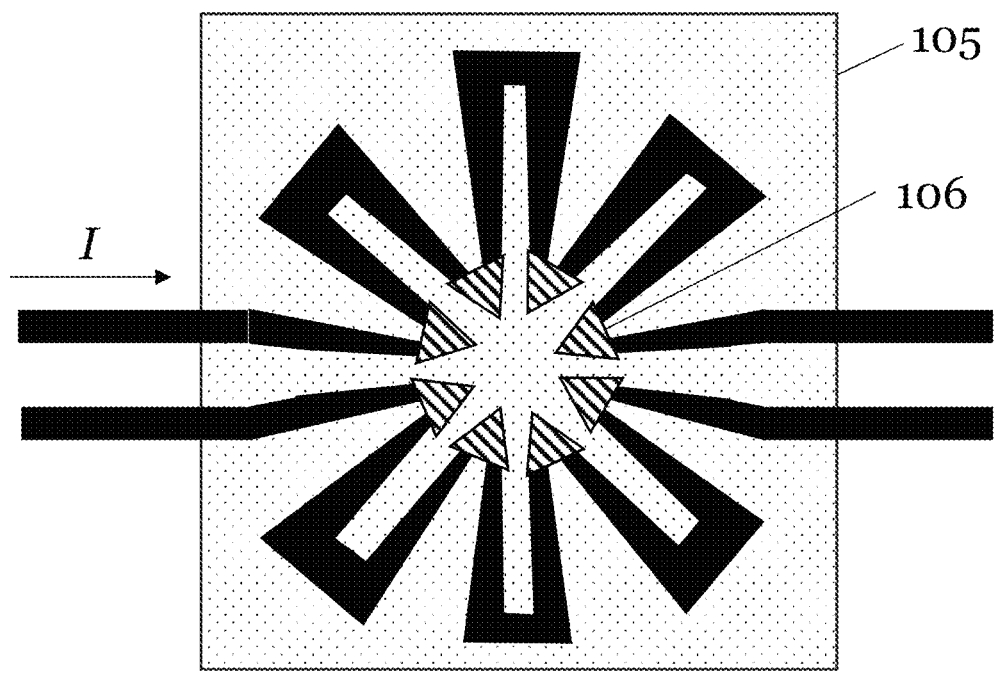
FIG. 14 illustrates a single micro-heater covered by a layer having nucleation cavities, according to example embodiments.

According to example embodiments, the micro-fluidic device further comprises a nonconductive layer 105 which is located, e.g. deposited, on top of the microbubble generator. In the following discussion, an example will be shown of a non-conductive layer 105 on top of a heating element 102. The non-conductive layer, may be the top layer which is in direct contact with the liquid. The non-conductive layer may be positioned on top of the capping layer. The non-conductive layer may have a thickness between 20-100 micrometer, e.g. 30 micrometer. Such an embodiment is illustrated in FIG. 14. The non-conductive layer may be at least a dielectric or a polymeric layer. The non-conductive layer 105 features a plurality of cavities 106 which are fabricated down to the heating element 102. The position of each cavity 106 is aligned with the position of a microstructure 104 of a micro-heater 103. For example, when using a heating element 102 with 100 micro-heaters 103, each micro-heater 103 having 10 microstructures 104; the non-conductive layer features 1000 cavities wherein each cavity is located above or aligned with a microstructure 104. The cavities 106 are through-holes or blind holes in the non-conductive layer 105. Thus, a liquid provided on the conductive layer 105 has access to the micro-heaters of the heating element or at least access to the shielding layer covering the micro-heaters.

In some embodiments, the provision of cavities above micro-heaters may contribute to the reduction of superheat. By providing cavities, the adequate temperature to generate microbubbles is lowered which allows faster creation of microbubbles. In applications such as flow cytometry a high throughput of cells is used. In such applications microfluidic devices as presented in this disclosure can be used to deflect characterized cells to different directions for sorting purposes. The faster the micro-fluidic device can generate microbubbles, the faster deflection of cells can be performed and the higher the throughput of the flow cytometry system can be.

It was observed that not only the presence of cavities in the neighborhood of microstructures contributes to the reduction of the superheat but also the shape of the cavities. It was observed that if the cavities feature a sharp corner, e.g. a corner smaller or equal than 90 degrees, after the generation of a first microbubble, small pockets of air remain or are trapped in this sharp corner of the cavity. It was determined that when generating further microbubbles, these small pockets contribute to the further reduction of the superheat because microbubbles may be easily generated from those trapped pockets of air at a lower temperature. According to example embodiments, the cross-section of the cavities may be triangular shaped. Such a geometrical shape may feature 3 sharp corners. Alternatively, the cross section may be rectangular shaped. Any cavity with a cross-sectional shape having at least one sharp corner is suitable for reducing the superheat. This further reduction of the superheat further contributes to lower power consumption and faster generation of microbubbles. As described above, this may be used in micro-fluidic systems for sorting cells.

According to example embodiments, the heating element 102 may be connected to a module that is configured to monitor parameters related to microbubble generation, for example it may be configured to monitor the temperature of the heating element 102. The module may be a sensor, e.g. an on-chip sensor, positioned and configured to sense the temperature of the heating element. Alternatively the heating element 102 may be connected to a module that is configured to monitor the resistance of the heating element 102. The module may be an electronic circuit electrically connected to the heating element and configured to measure the resistance of the heating element. The temperature of the heating element or the thermal resistance of the heating element may be monitored, for example when a voltage or current pulse is applied to the heating element. This allows the voltage pulse, which is used to bring the heating element to the adequate temperature, to be adjusted to the actual condition of the heating element. This improves the accuracy of the micro-fluidic device. Also, power consumption can be further reduced. The current and resistance of the heating element may be simultaneously monitored in some embodiments.

A power unit adapted to the microbubble generator (e.g. a current source, either constant, variable or even alternate) may be integrated in some embodiments, for example for in-field applications such as in-situ studies, or connections may be provided for connecting the unit to an external source.

Second Embodiment

Other embodiments may be adapted to generate microbubbles by other methods, such as for instance by electrolysis. The microbubble generator may comprise an electrolytic unit, comprising at least one set of electrodes as microbubble generating element. Each set of electrodes is adapted for generating a plurality of microbubbles, for example by the shape of microstructures present in the set of electrodes. A set of electrodes comprise at least two electrodes adapted to produce electrolysis when a potential difference (voltage) is applied between the at least two electrodes of the set. In such cases, the connections of the microbubble generating elements may be adapted to create a voltage in a set of electrodes, e.g. between at least two electrodes, comprising microstructures, hence creating electrolysis in the liquid in contact therewith, and producing microbubbles. For example, the microbubbles may comprise oxygen and hydrogen if the liquid comprises water.

Figure 4:
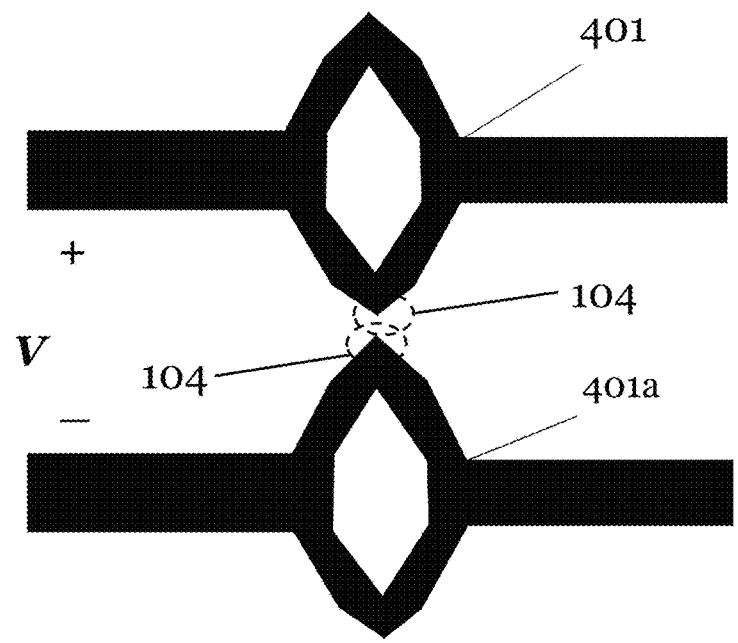
FIG. 4 illustrates an electrode couple, according to example embodiments.

FIG. 4 shows a system comprising a set of electrodes, in this case two electrodes 401, 401a using the same lip-shaped structures as in FIG. 3 or FIG. 13, which may also comprise microstructures 104. Each of the two electrodes is connected to a voltage of opposite polarity (or to a positive voltage and to ground, respectively), obtaining a potential difference between the tip of the microstructure 104 of one electrode 401 and the tip of the microstructure 104 of the other electrode 401a. This potential difference, which can be variable, may be used to produce microbubbles by electrolysis of the fluid. This system may present low power consumption for producing microbubbles, for example gas microbubbles (e.g. hydrogen and oxygen in case of aqueous fluids).

Figure 11:
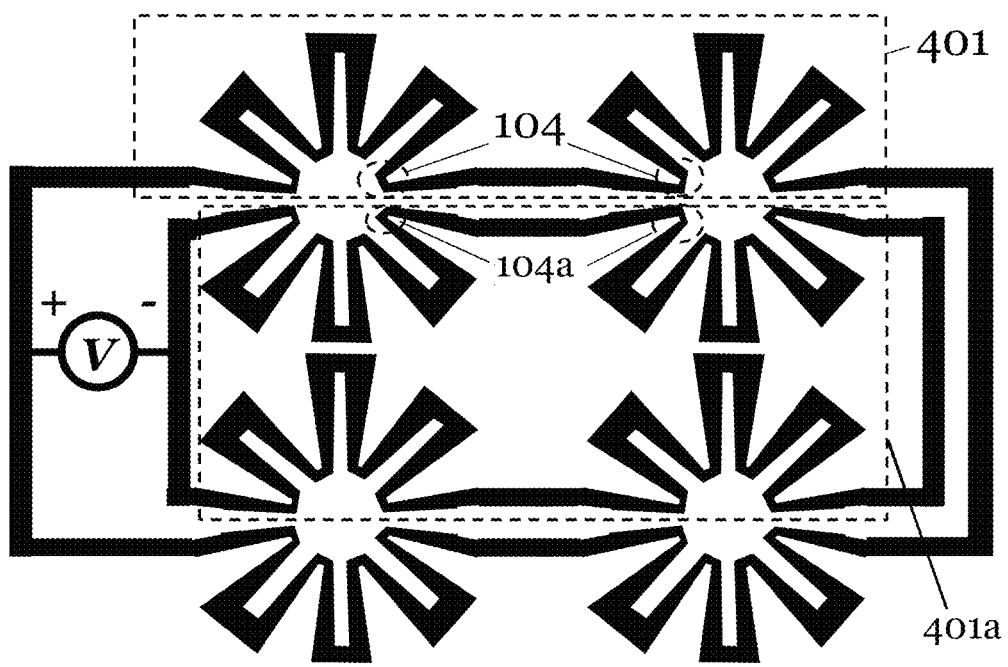
FIG. 11 illustrates a matrix of electrodes of an electrolytic unit, according to example embodiments.

A plurality of sets of electrodes may be positioned in rows, adapting the connections so that if one row of electrodes is connected to a first electric potential, the following (neighboring) row is connected to the opposite electric potential, hence creating a voltage between the rows and generating microbubbles via electrolysis. The size of the microbubble may be controlled by controlling the voltage, thereby contributing to increased controllability of a jet force created by the micro-fluidic device. The electrodes may have the same shape as the micro-heaters of the first embodiment, for example lip-shaped, or a circular meander shaped structure having a plurality of microstructures as shown in the FIG. 11.

Other features, analogous to the features of the embodiments comprising heating elements, may be applicable to embodiments comprising electrolytic units. For example, the artifacts observed in the microstructures of the heating elements may also apply to electrolytic units or to any other way of microbubble generation, the artifacts being nucleation sites for microbubbles (formed by electrolysis). The non-conductive layer 105 with shaped cavities 106 of FIG. 14 can also be applied to a microfluidic device comprising an electrolytic unit. A monitoring module may also be included, the module being configured to monitor the voltage of an electrolytic unit, or the capacitance, or the current, or variations thereof, hence determining the presence of microbubbles and controlling their growth. Voltage may be provided as a static or variable voltage.

Figure 15:
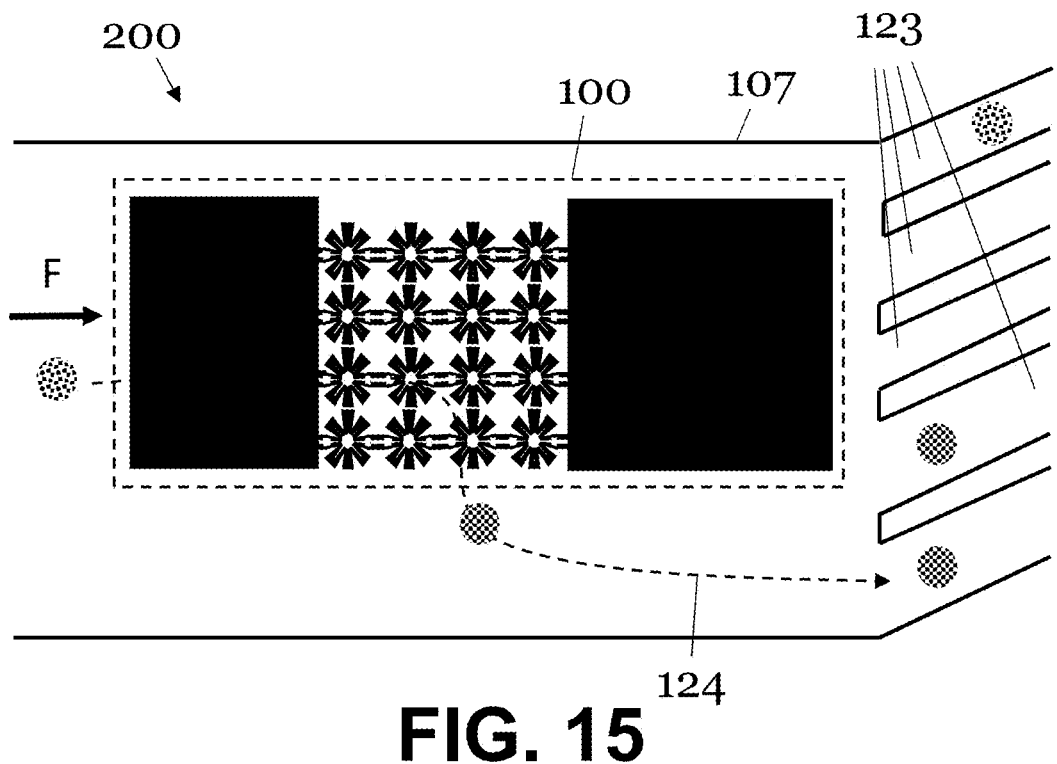
FIG. 15 illustrates a system for sorting cells, according to example embodiments.

In a second aspect, systems 200 for sorting cells are presented. The systems described in the second aspect may be used to sort any object which fits in the micro-fluidic channels of such systems. An embodiment of such a system is illustrated in FIG. 15. The system comprises a microfluidic channel 107 for providing and propagating cells. The system 200 may be a flow cytometry device wherein cell identification is performed based on the fluorescence of objects or based on recorded images of cells (e.g. holograms) propagating in the micro-fluidic channel.

The system 200 comprises a micro-fluidic device 100 as described in the first aspect. The micro-fluidic device 100 may be positioned in the micro-fluidic channel 107 of the system. Such an embodiment is illustrated in FIG. 15. The micro-fluidic device 100 may be positioned on any inner wall of the micro-fluidic channel 107, ensuring that there is direct contact between the liquid and the micro-fluidic device 100. For example, it may be positioned in the walls belonging to the closure lid of the micro-fluidic device. The micro-fluidic device 100 is positioned with respect to the micro-fluidic channel 107 such that deflection of single cells propagating or flowing in the micro-fluidic channel 107 can be performed by generating microbubbles inside the micro-fluidic channel 107 of the system 200, wherein the jet flow (F) created in the micro-fluidic channel 107 by generated microbubbles deflects cells. The cells may be deflected such that they are directed towards different outlets 123 which are fluidically connected to the micro-fluidic channel 107. The compact design of the micro-fluidic device 100 may allow integration into (inside) the micro-fluidic channel 107 of the system 200. This may permit highly parallelized flow cytometry devices because the complete system can be integrated on a small area of a chip. In FIG. 15 it is also noticed that the micro-fluidic channel 107 is wider than the width of the micro-fluidic device 100. This is used because the micro-fluidic device 100 creates a jet flow in the micro-fluidic channel 107 which deflects the cell towards another location in the micro-fluidic channel where no micro-fluidic device 100 is active. Hence, the propagation path of an object in the micro-fluidic channel 107 is changed to a different propagation path (propagation path of the object being indicated with an arrow 124). To allow this, the wider micro-fluidic channel 107 is used. In such an embodiment, the micro-fluidic device 100 would not be activated if the propagation path of an object leads to the correct outlet. When the propagation path of an object does not lead to the correct outlet, the micro-fluidic device 100 is activated.

According to example embodiments, the substrate 101 of the micro-fluidic device 100 may be comprise at least part of an inner wall of the micro-fluidic channel 107 of the system 200 for sorting cells.

Figure 16:
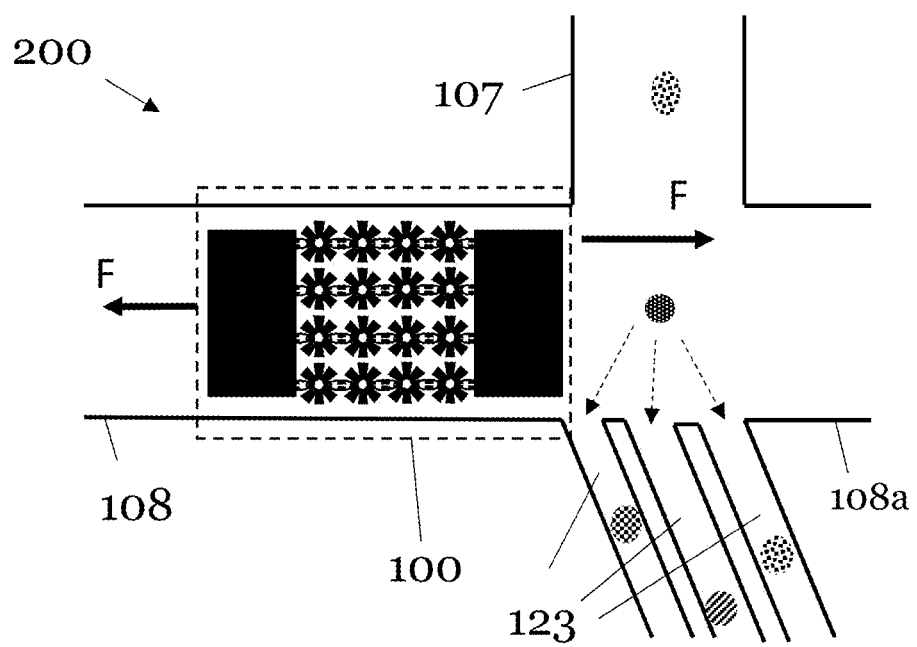
FIG. 16 illustrates a system for sorting cells, according to example embodiments.
Figure 17:
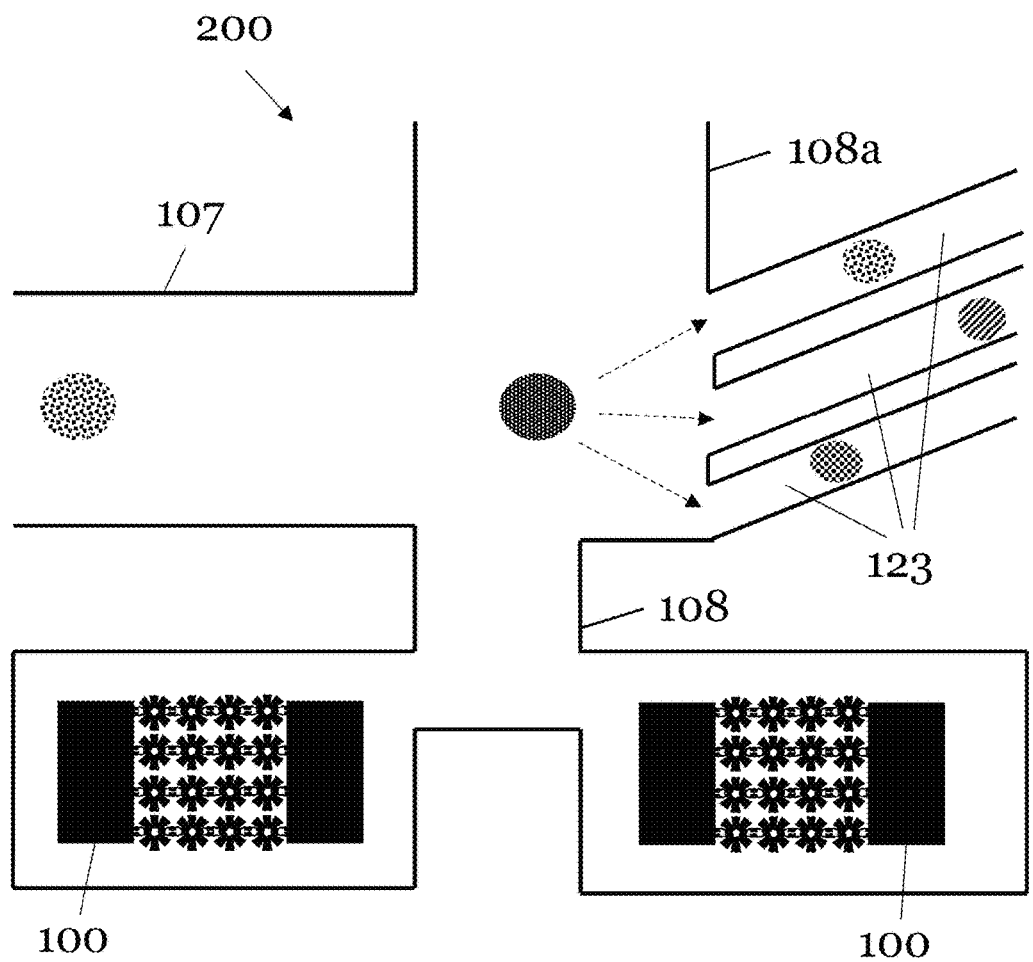
FIG. 17 illustrates an embodiment with two micro-fluidic devices implementing a jet flow regime, according to example embodiments.

According to another embodiment, a system 200 for sorting cells may comprise a first micro-fluidic channel 107 for propagating cells which is fluidically connected to a second micro-fluidic channel 108. Such an embodiment is illustrated in FIG. 16. The first micro-fluidic channel 107 and the second micro-fluidic channel 108 may be fluidically crossing each other. The second micro-fluidic channel 108 may be positioned perpendicular to the first micro-fluidic channel 107. The impact of the generated jet flow perpendicular on the propagation path of a cell in the first micro-fluidic channel is thereby maximal. For example, power usage may be reduced. The micro-fluidic device 100 may be positioned in the second microfluidic channel 108 as illustrated in FIG. 16. A jet flow created in the second microfluidic channel 108 deflects single cells which are propagating through the first micro-fluidic channel 107, towards an outlet 123 of the first micro-fluidic channel 107. Such a design allows using a large microfluidic device 100 in a wide fluidic channel or chamber 108, than for example a more narrow channel 107 can accommodate. The second micro-fluidic channel may also comprise at least two micro-fluidic devices as illustrated in FIG. 17.

According to example embodiments, the system 200 for sorting cells may comprise a plurality of micro-fluidic devices 100 positioned in or on an inner wall of the micro-fluidic channel 107 used to propagate cells. Alternatively they are positioned in other micro-fluidic channels fluidically connected to the micro-fluidic channel 107. Such embodiments contribute to the usability of the system.

Figure 18:
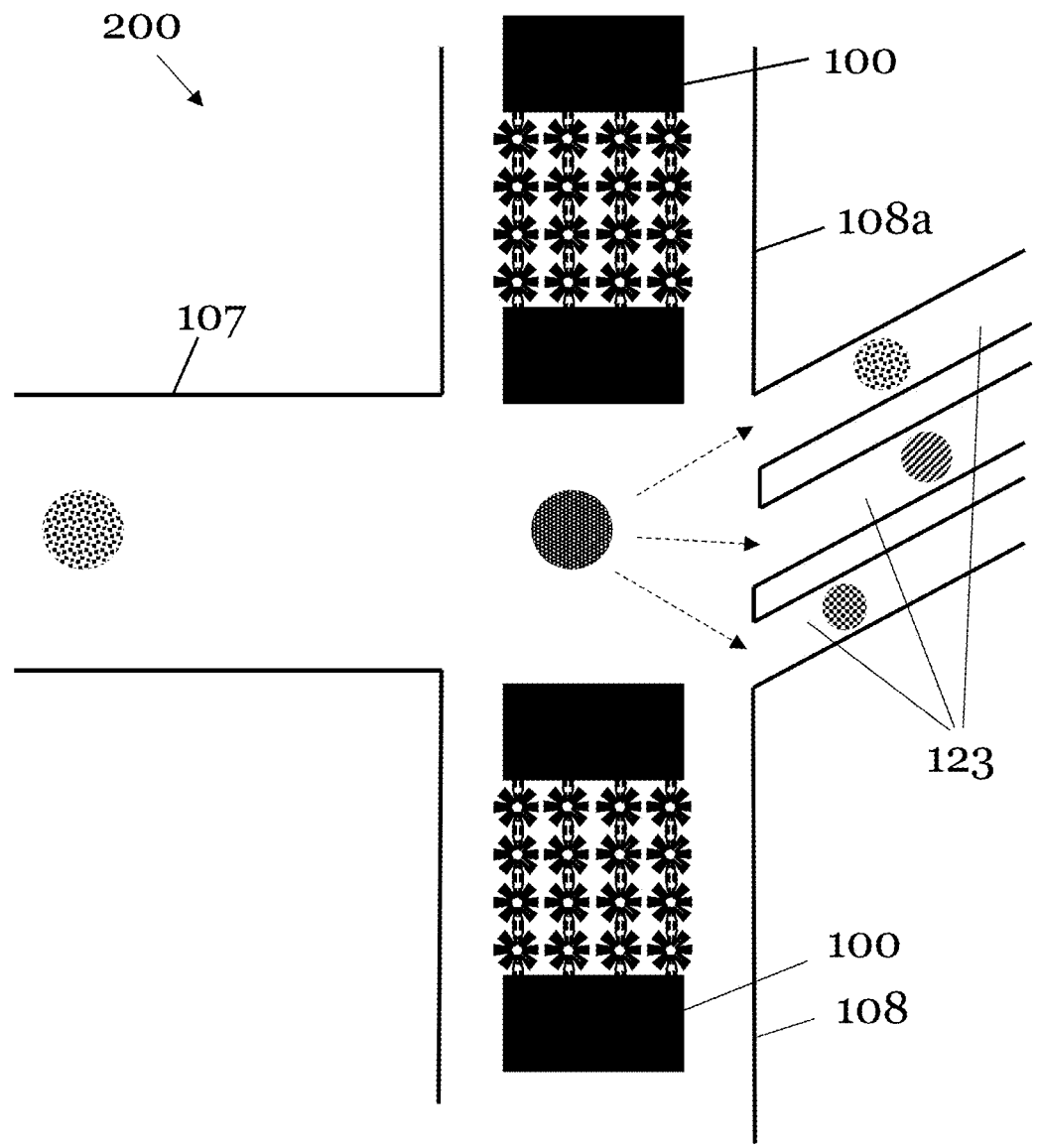
FIG. 18 illustrates an alternative embodiment with two micro-fluidic devices implementing a jet flow regime, according to example embodiments.

According to another embodiment, a system 200 for sorting cells may comprise a first micro-fluidic channel 107 for propagating cells which is fluidically connected to a second 108 and a third micro-fluidic channel 108a. Such an embodiment is illustrated in FIG. 18. The first, second and third microfluidic channel 107, 108, 108a may be fluidically crossing each other. The second and third micro-fluidic channel 108, 108a may be positioned perpendicular to the first micro-fluidic channel 107. The second and third micro-fluidic channel 108, 108a may be fluidically connected to the first micro-fluidic channel 107 at opposite sides of the first micro-fluidic channel 107. The impact of a generated jet flow perpendicular on the propagation path of a cell in the first micro-fluidic channel 107 is thereby maximal. In some embodiments, power usage may be reduced. A first micro-fluidic device 100 may be positioned in the second micro-fluidic channel 108. A jet flow created in the second micro-fluidic channel 108 deflects single cells which are propagating through the first micro-fluidic channel 107, towards an outlet 123 of the first micro-fluidic channel 107. A second micro-fluidic device 100 may be positioned in the third micro-fluidic channel 108a. A jet flow created in the third micro-fluidic channel 108a deflects single cells which are propagating through the first microfluidic channel 107, towards an outlet 123 of the first micro-fluidic channel 107. Such systems allow precise control over the magnitude of the force on cells in the first micro-fluidic channel 107, generated by the jet flow. Hence, the accuracy of the sorting may be increased. Also, when two or more micro-fluidic devices conjointly create the jet flow, power of used in each micro-fluidic device can be reduced because the jet flow is created by two or more micro-fluidic devices. Hence, smaller bubbles may be generated, enabling faster generation of the jet flow.

According to example embodiments, a system 200 for sorting cells comprising a microfluidic channel and at least two micro-fluidic devices 100 as described in the first aspect is presented. The at least two micro-fluidic devices may be positioned and configured to synchronously deflect single cells propagating in the micro-fluidic channel. In some embodiments, by synchronizing multiple micro-fluidic devices for simultaneously deflecting a single cell, the sorting accuracy can be improved.

Figure 19:
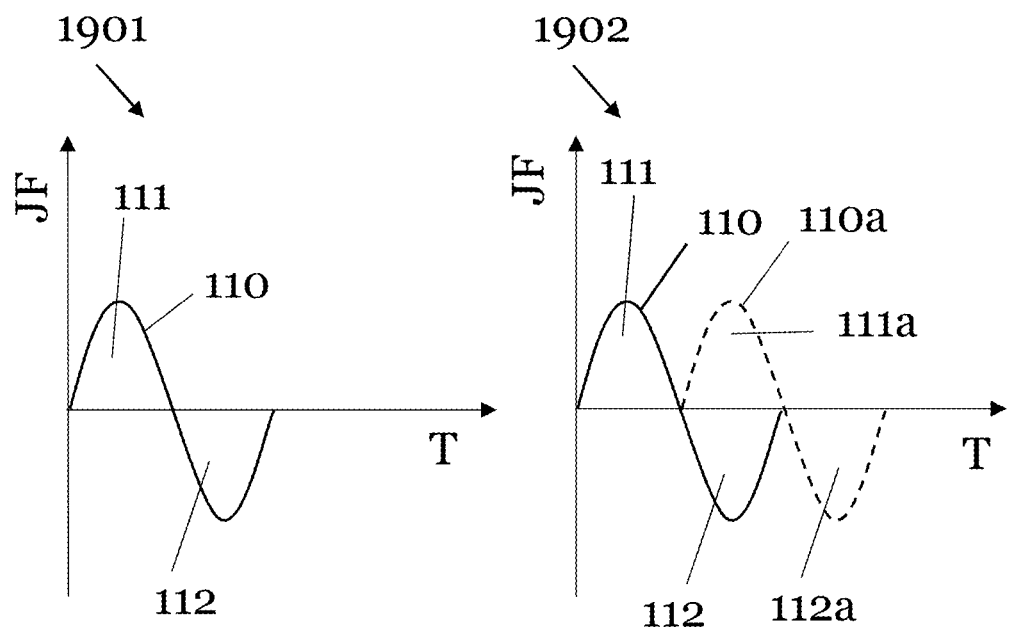
FIG. 19 illustrates a jet flow regime of a single microfluidic device and of two micro-fluidic devices, according to example embodiments.

Every jet 5 flow is composed of two phases: 1) a PUSH phase when microbubbles are created (for example, vapor microbubbles may be thermally created) that eject an outbound jet flow and 2) a PULL phase when microbubbles collapse and retract an inbound jet flow. FIG. 19 illustrates the diagrams 1901, 1902 of a jet flow generation cycle for example embodiments comprising one and two micro-fluidic devices, respectively. Diagram 1901 for a single micro-fluidic device shows a jet flow (JF) generation cycle 110 with the push phase 111 and the pull phase 112 as a function of time (T). Either one of the regimes can be used for sorting, dependent on the timing set by the user. A problem arises when two propagating cells in the microfluidic channel 107 are too close to each other. In such a situation, after pushing the first cell, the second cell may inevitably run into the PULL regime. As a result the second cell is wrongfully deflected to the wrong outlet. To overcome this, a further micro-fluidic device may be positioned and configured such that the force created by both micro-fluidic device may cancel out each other.

For example, one of the micro-fluidic devices may be configured to activate with a half cycle phase delay from the other micro-fluidic device. This allows delay of the pull mode by half a period. In this way, this cell is not wrongly sorted. Diagram 1902 of FIG. 19 illustrates jet flow generation cycles 110, 110a of two micro-fluidic device with a push phase 111, 111a and a pull phase 112, 112a, with a half a cycle delay phase. The delay phase causes the pull phase 112 of one micro-fluidic device to coincide with the push phase 111a of the other micro-fluidic device thereby cancelling any force. Therefore, the jet flow is nearly zero in this overlapping half cycle which precludes the wrong deflection of closely following cells after the cells to be sorted. The jet flow generation cycles as depicted in the diagram 1902 of FIG. 19 is suitable for microfluidic devices which are positioned at the same side of a micro-fluidic channel. For example, when implemented in the system of FIG. 16, two micro-fluidic devices 100 are located in the micro-fluidic channel 108, at the same side of the micro-fluidic channel 107. This is illustrated in FIG. 17.

Figure 20:
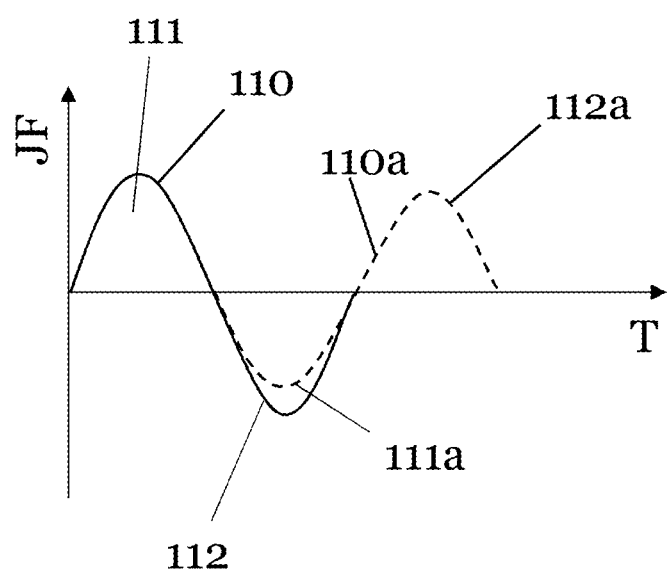
FIG. 20 illustrates a jet flow regime of two micro-fluidic devices, according to example embodiments.

Another embodiment is illustrated in FIG. 20. In this embodiment the PULL phase of the first microfluidic device coincides with the PUSH phase of the second micro-fluidic device, and both align in the same physical direction at this moment. Consequently, the total jet flow is reinforced. This embodiment will work most effectively when the two microdevices are placed on opposite sides of the micro-fluidic channel 107. For example, when implemented in the system of FIG. 16, two micro-fluidic devices are located in the microfluidic channel 108, at the opposite sides of the micro-fluidic channel 107. This is illustrated in FIG. 18.

According to a third aspect, a method for fabrication of a micro-fluidic device as described in embodiments of the first aspect is presented. The micro-fluidic device may be fabricated using common micro-fluidic manufacture routes, e.g. semiconductor fabrication technology. For example, the micro-fluidic device may be fabricated using CMOS compatible processing steps. The method comprises providing a substrate and providing a conductive layer, e.g. a metal layer, on top of the substrate. The substrate may be a semiconductor substrate, e.g. a silicon substrate. The substrate may also be a glass substrate. The conductive layer may for example be an aluminum, copper or tungsten layer. The conductive layer may for example be formed by a stack of conductive layers, such as a Ti 20/AlCu 200/TiN 100 (nm) stack, or a Ti 15/TiN 10/W 100/TiN 100 (nm) stack. Thereafter, a microbubble generator is created by patterning the conductive layer. The creation of the microbubble generator comprises the patterning of at least one microbubble generating element in that conductive layer. For example, the patterning of the at least one micro-heater for a heating element 103 as microbubble generator comprises patterning a series of connected microstructures 104 in the conductive layer. Each microstructure 104 is fabricated such that its shape can generate a microbubble when the heating element 101, and consequently each micro-heater, heats up. The fabrication of each microstructure is performed such that each microstructure comprises a portion with a dimension, e.g. the width or height, of 10 micrometers or smaller and that the rest of the micro-heater has dimensions, e.g. the width or height, greater than 10 micrometers to ensure that a microbubble is only generated at the location of the microstructure. Likewise, a patterning of at least one set of electrodes for an electrolytic unit as microbubble generator may comprise patterning a series of connected microstructures in the conductive (e.g. metal) layer, with such a shape that they can generate a microbubble when inducing a voltage between the electrodes. The method of fabrication of the at least one set of electrodes, and the shape and dimension thereof may be the same as for micro-heaters, and the electrical connections may be adapted for the generation of a voltage between the microstructures, rather than flowing a current through the microstructures.

According to an embodiment, the patterning of the at least one microbubble generation element, e.g. micro-heater, may further comprise patterning another series of connected microstructures. Such a device is described in the first aspect. The patterning of a single microbubble generation element, e.g. micro-heater, may comprise the patterning of at least two microstructures which are electrically connected in parallel. The patterning may further comprise the patterning of a series of single microbubble generation element, e.g. micro-heaters, which are electrically connected in series. For example, the patterning may further comprise the patterning of a plurality of different series of microbubble generation elements, e.g. micro-heaters, which are electrically connected in series and wherein the different series are connected in parallel.

According to an embodiment, the method may further comprise creating a capping layer on top of the microbubble generator, e.g. heating element or electrolytic unit. The presence of the capping layer increases the robustness of the microbubble generator because it fixes the microbubble generator and ensures that deformation of the microbubble generator during usage is minimal or none. In an electrolytic unit as microbubble generator, the capping layer may protect the conductive structure. In some embodiments, the life-time of the device may be increased. As explained in the first aspect, when several voltage or current pulses are applied to the microbubble generator, more particularly to the one or more microbubble generating elements thereof, deformation of the microstructures is observed (see FIG. 12). When the deformation is unwanted, it can be avoided by depositing a capping layer on top of the microbubble generator, e.g. heating element or electrolytic unit. Such a capping layer may comprise a SiC layer. The SiC layer may have a thickness between 20 nm and 2 micrometers, for example, 50 nm. The capping layer may further comprise a SiN layer wherein the SiN layer is in direct contact with the microbubble generator, e.g. heating element or electrolytic unit, and wherein the SiC layer is deposited on top of the SiN layer. In such an embodiment, the SiC layer is in direct contact with the liquid when provided. The SiN layer functions as electrical insulator. The capping layer may be deposited before a micro-fluidic channel is formed on top of the microbubble generator, e.g. heating element or electrolytic unit; thus, before e.g. a photo-patternable material is deposited on the microbubble generator.

According to example embodiments, the method may further comprises creating a nonconductive layer on top of the microbubble generator, e.g.; heating element or electrolytic unit, and creating cavities 106 in the layer at the location of patterned microstructures 104. The cavities 106 may be triangular shaped or rectangular shaped. Each cavity may be created such that it comprises at least one sharp corner, as described in the first aspect.

Figure 21:
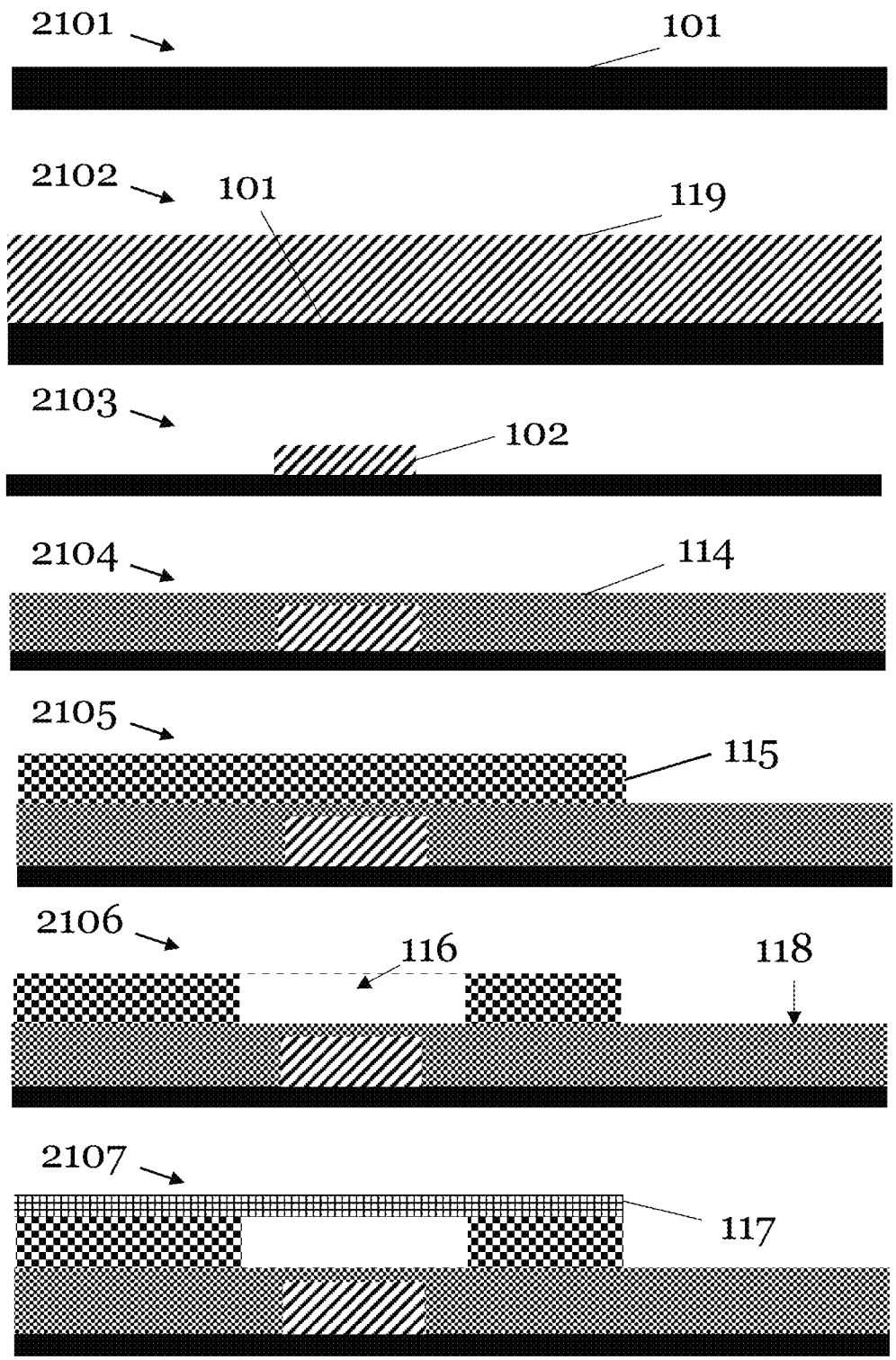
FIG. 21 illustrates a process flow for creating a micro-fluidic device, according to example embodiments.

FIG. 21 illustrates a specific embodiment of the third aspect. A method (comprising seven steps 2101-2107) to fabricate the micro-fluidic device 100 having a closed micro-fluidic component is illustrated. The steps are disclosed for a heating element 102 comprising micro-heaters, but it could be applied to any other microbubble generator such as an electrolytic unit comprising at least one set of electrodes. The micro-fluidic device 100 is fabricated by providing 2101 a substrate 101, for example a semiconductor substrate such as e.g. a silicon substrate. On the substrate, a heating element 102 is created, for example by first providing 2102 a conductive layer, such as a metal layer 119 and patterning 2103 that metal layer 119. After fabrication of the heating element 102, a shielding layer 114 is deposited 2104 on top of the substrate 101 thereby covering the heating element 102. The heating element 102 may be covered completely by the shielding layer 114. The shielding layer 114 may be an insulating layer; it may comprise $SiO_2$, SiN or a mixture thereof. On top of the shielding layer 114, a micro-fluidics layer 115 is provided 2105. The micro-fluidics layer 115 may be fabricated from a patternable material suitable for micro-fluidic applications. The material may be PDMS or a photo-patternable adhesive suitable for wafer-level microfluidic structure fabrication. In some embodiments, the material of the micro-fluidics layer 115 may be adapted to provide a strong bonding with the shielding layer 114. If the shielding layer 114 comprises $SiO_2$ or SiN, the material is selected such that a strong bond with $SiO_2$ or SiN can be realized. Thereafter, the micro-fluidics layer 115 is patterned 2106 to create the micro-fluidic components 116 in the layer 115. The micro-fluidics layer 115 is patterned 2106 such that the location of the micro-fluidics component 116 is in vicinity of the heating element 102 to allow heating of a liquid when present in the micro-fluidics component 116. For example, the heating element 102 is located below the micro-fluidic component 116. In other words, the heating element 102 may be aligned with the micro-fluidic component 116. In an optional final step, the micro-fluidics component 116 may be closed 2107 with a lid 117, e.g. glass or polymer (such as polycarbonate, cyclic olefin polymer/copolymer, polypropylene) lid. Thus, the closing lid 117 is attached to the micro-fluidics layer 115 in any suitable way, for example by flip-chip bonding, anodic bonding, thermally or solvent-based polymer bonding, PDMS-Si/glass bonding or simply by adhesive tapes. When using a photo-patternable adhesive, the material may be used to pattern the micro-fluidic component 116. In addition to that, the photo-patternable adhesive may be used to attach the closing lid 117. This dual functionality contributes to the simplicity of fabricating the device. Alternatively or additionally, the closing lid may comprise a micro-fluidics device 100, which may also be obtained according to embodiments of the present method.

Figure 22:
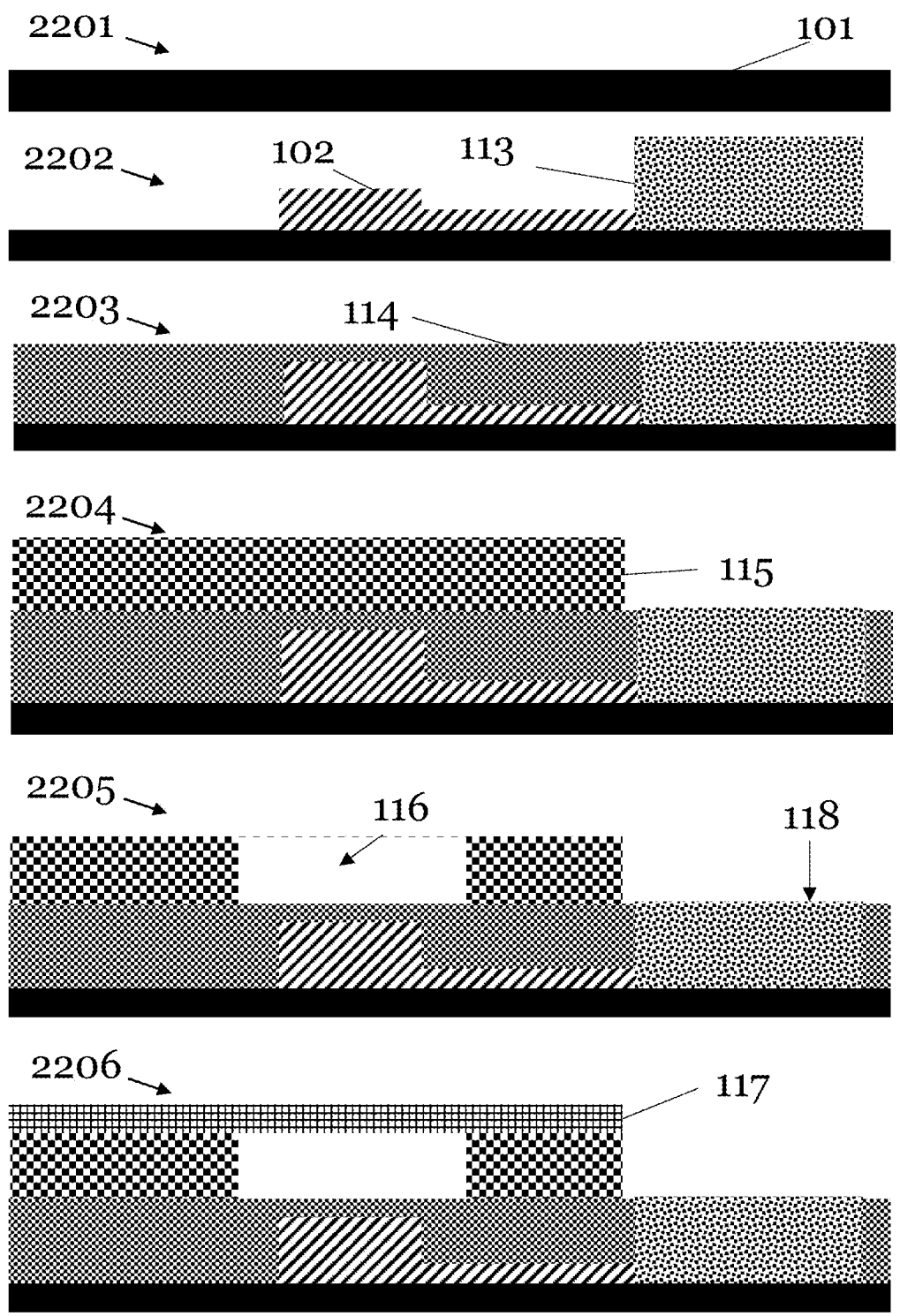
FIG. 22 illustrates a process flow for creating a micro-fluidic device, according to example embodiments.

FIG. 22 illustrates a specific embodiment of the third aspect. A method (comprising six steps 2201-2206) to fabricate the micro-fluidic device 100 having a closed micro-fluidic component and a bondpad for supplying a voltage pulse to the heating element as microbubble generator is presented. The micro-fluidic device is fabricated by providing 2201 a substrate 101, for example a semiconductor substrate such as e.g. a silicon substrate. On the substrate, the heating element 102 is created 2202, for example by first providing a conductive, e.g. metal, layer and patterning that conductive layer. Additionally, on the substrate 101 a bondpad 113 is created. The bondpad 113 is created such that it is in electrical contact with the heating element 102. For this purpose, the heating element 102 and the bondpad 113 may be fabricated from the same conductive layer. In some embodiments, in a single patterning step, both the heating element 102 and the bondpad 113 may be created 2202. Alternatively, if the material of the bondpad 113 is different from the material of the heating element 102, a different patterning step(s) may be used to create the bondpad 113. Further, the bondpad 113 may be in electrical contact with the heating element 102. After fabrication of the heating element 102 and the bondpad 113, a shielding layer 114 is deposited 2203 on top of the substrate 101 thereby covering the heating element 102. The bondpad 113 is also covered by the shielding layer; however, its top surface 118 is not covered to allow later electrical connections to a power supply. The shielding layer 114 may comprise $SiO_2$ or SiN, for example. On top of the shielding layer, a micro-fluidics layer 115 is provided 2204. The micro-fluidics layer 115 is positioned such that is does not cover the top surface 118 of the bondpad 113. The micro-fluidics layer 115 may be fabricated from a patternable material suitable for micro-fluidic applications. The material may be PDMS, SU8 or a photo-patternable adhesive suitable for wafer-level micro-fluidic structure fabrication. It should be ensured that the material of the micro-fluidics layer 115 is adapted to provide a strong bond with the shielding layer 114. If the shielding layer 114 is a $SiO_2$ or SiN layer, the material is selected such that a strong bond with $SiO_2$ or SiN can be realized. Thereafter, the micro-fluidics layer 115 is patterned 2205 to create the micro-fluidic component 116 in the layer 115. The micro-fluidics layer 115 is patterned 2205 such that the location of the micro-fluidics component 116 is in vicinity of the heating element 102 to allow heating of a liquid when present in the micro-fluidics component 116. For example, the heating element 102 is located below the micro-fluidic component 116. In other words, the heating element 102 may be aligned with the micro-fluidic component 116. In an optional final step, the micro-fluidics component 116 may be closed 2206 with or attached to a lid 117, e.g. glass lid. The closing lid 117 may be bonded to the micro-fluidics layer 115. The micro-fluidics component 116 is closed 2206 thereby not covering the bondpad 113 to allow direct electrical connectivity to a power supply later on. The step of closing the micro-fluidic component 116 is performed for example by flip-chip bonding, anodic bonding, thermally or solvent-based polymer bonding, PDMS-Si/glass bonding or simply by adhesive tapes. In some embodiments, when using a photo-patternable adhesive, the material may be used to pattern the micro-fluidic component 116. In addition to that, the photo-patternable adhesive may be used to attach the closing lid 117. This dual functionality contributes to the simplicity of fabricating the device.

The invention claimed is:

1. A micro-fluidic device for deflecting objects in a liquid, the device comprising:
    a substrate for providing an object-containing liquid thereon; and
    a microbubble generator comprising at least one microbubble generating element,
    wherein the microbubble generator is located on a surface of the substrate and in direct contact with the object-containing liquid when the object-containing liquid is provided on the substrate,
    wherein the at least one microbubble generating element is configured to deflect a single object in the object-containing liquid through generation of a plurality of microbubbles,
    wherein the at least one microbubble generating element comprises a first series of connected microstructures, and
    wherein each of the connected microstructures is configured to generate a microbubble in the object-containing liquid when the microbubble generator is powered.

2. The micro-fluidic device according to claim 1,
    wherein the microbubble generator is a heating element,
    wherein the at least one microbubble generating element comprises at least one micro-heater, and
    wherein the at least one micro-heater is shaped such that at least two of the connected microstructures heat up simultaneously when an electrical current flows through the at least one micro-heater.

3. The micro-fluidic device according to claim 2,
    wherein the at least one micro-heater is a circular meander shaped structure, and
    wherein the at least two connected microstructures are electrically connected in parallel.

4. The micro-fluidic device according to claim 1,
    wherein the microbubble generator is a heating element,
    wherein the at least one microbubble generating element comprises at least one micro-heater,
    wherein the at least one micro-heater further comprises a second series of connected microstructures connected in parallel to the first series of connected microstructures, and
    wherein the at least one micro-heater is shaped such that at least two microstructures of different series of connected microstructures heat up simultaneously when an electrical current flows through the at least one micro-heater.

5. The micro-fluidic device according to claim 1,
    wherein the microbubble generator is an electrolytic unit comprising at least a set of electrodes,
    wherein the electrodes are shaped such that at least two microstructures generate microbubbles simultaneously when a voltage is applied to the electrodes.

6. The micro-fluidic device according to claim 1, further comprising a non-conductive layer located in between the object-containing liquid and the microbubble generator when the object-containing liquid is provided on the substrate,
    wherein the non-conductive layer comprises a plurality of cavities fabricated down to the microbubble generator, and
    wherein each of the plurality of cavities is aligned with a corresponding one of the connected microstructures.

7. The micro-fluidic device according to claim 6, wherein one of the plurality of cavities comprises at least one sharp corner.

8. The micro-fluidic device according to claim 6, wherein a cross-section, parallel to the substrate, of one of the plurality of cavities is triangular shaped or rectangular shaped.

9. The micro-fluidic device according to claim 1, wherein each of the connected microstructures comprises a portion having a cross-sectional dimension of 10 micrometers or smaller.

10. The micro-fluidic device according to claim 1, wherein the microbubble generator is a heating element, wherein the microbubble generator comprises only one metal layer.

11. The micro-fluidic device according to claim 1, further comprising a controller connected to the microbubble generator, wherein the controller is configured to monitor at least one parameter of the microbubble generator related to the generation of microbubbles.

12. The micro-fluidic device according to claim 11,
wherein the microbubble generator is a heating element,
wherein the at least one microbubble generating element is at least one micro-heater,
wherein the controller is configured to monitor a temperature of the heating element or configured to monitor a resistance of the heating element.

13. The micro-fluidic device according to claim 1, wherein the microbubble generator further comprises a SiC layer for preventing deformation of the microbubble generator.

14. A system for sorting objects comprising:
a first micro-fluidic device for deflecting objects in a liquid, comprising:
a substrate for providing an object-containing liquid thereon; and
a microbubble generator comprising at least one microbubble generating element,
wherein the microbubble generator is located on a surface of the substrate and in direct contact with the object-containing liquid when the object-containing liquid is provided on the substrate,
wherein the at least one microbubble generating element is configured to deflect a single object in the object-containing liquid through generation of a plurality of microbubbles,
wherein the at least one microbubble generating element comprises a first series of connected microstructures, and
wherein each of the connected microstructures is configured to generate a microbubble in the object-containing liquid when the microbubble generator is powered; and
a first micro-fluidic channel,
wherein the first micro-fluidic device is positioned to deflect single objects propagating in the first micro-fluidic channel by generating microbubbles.

15. The system according to claim 14, further comprising a second micro-fluidic channel fluidically connected to the first micro-fluidic channel,
wherein the first micro-fluidic device is positioned in the second micro-fluidic channel and configured for deflecting single objects propagating in the first micro-fluidic channel by generating microbubbles.

16. The system according to claim 15, further comprising:
a third micro-fluidic channel fluidically connected to the first micro-fluidic channel,
wherein the second micro-fluidic channel and the third micro-fluidic channel are aligned and positioned at opposite sides of the first micro-fluidic channel;
a second micro-fluidic device positioned in the third micro-fluidic channel,
wherein the first micro-fluidic device and the second micro-fluidic device are configured to deflect single objects propagating in the first micro-fluidic channel.

17. A method for fabricating a micro-fluidic device for deflecting objects in a liquid, the method comprising:
providing a substrate;
providing a conductive layer on top of the substrate; and
patterning a microbubble generator comprising at least one microbubble generating element in the conductive layer,
wherein patterning the microbubble generator comprises patterning a series of connected microstructures, and
wherein each of the connected microstructures is configured to generate a microbubble when the microbubble generator is powered.

18. The method according to claim 17, wherein patterning the microbubble generator comprising at least one microbubble generating element comprises fabricating the at least one microbubble generating element such that its shape allows at least two microstructures of the at least one microbubble generating element to generate microbubbles simultaneously when the at least one microbubble generating element is activated.

19. The method according to claim 18, wherein patterning the microbubble generator comprising at least one microbubble generating element further comprises patterning at least one micro-heater such that its shape allows at least two microstructures of the at least one micro-heater to heat up simultaneously when an electrical current flows through the at least one micro-heater.

20. The method according to claim 18, wherein patterning the microbubble generator comprising at least one microbubble generating element comprises patterning at least one set of electrodes such that its shape allows at least two microstructures of the at least one set of electrodes to create electrolysis simultaneously when a voltage is applied to the at least one set of electrodes.

* * * * *